US010357162B1

(12) United States Patent
Dutta

(10) Patent No.: US 10,357,162 B1
(45) Date of Patent: Jul. 23, 2019

(54) IMAGING SYSTEM FOR SCREENING AND DIAGNOSIS OF BREAST CANCER

(71) Applicant: Banpil Photonics, Inc., Santa Clara, CA (US)

(72) Inventor: Achyut Kumar Dutta, Sunnyvale, CA (US)

(73) Assignee: Banpil Photonics, Inc., Santa Clara, CA (US)

( * ) Notice: Subject to any disclaimer, the term of this patent is extended or adjusted under 35 U.S.C. 154(b) by 163 days.

(21) Appl. No.: 14/984,717

(22) Filed: Dec. 30, 2015

(51) Int. Cl.
*A61B 5/00* (2006.01)

(52) U.S. Cl.
CPC .......... *A61B 5/0091* (2013.01); *A61B 5/0013* (2013.01); *A61B 5/708* (2013.01); *A61B 5/7246* (2013.01); *A61B 5/742* (2013.01); *A61B 2560/0425* (2013.01)

(58) Field of Classification Search
CPC ........ A61B 5/0084; A61B 5/0059; A61B 5/00
See application file for complete search history.

(56) References Cited

U.S. PATENT DOCUMENTS

| | | | |
|---|---|---|---|
| 2004/0215101 A1* | 10/2004 | Rioux | A61B 90/14 600/562 |
| 2012/0209124 A1* | 8/2012 | Shieh | A61B 5/0091 600/476 |
| 2012/0296205 A1* | 11/2012 | Chernov | A61B 18/1445 600/431 |
| 2013/0178735 A1* | 7/2013 | Iddan | A61B 5/0066 600/425 |
| 2013/0253322 A1* | 9/2013 | Suzuki | A61B 8/406 600/443 |
| 2014/0276017 A1* | 9/2014 | Sproul | A61B 5/7475 600/425 |
| 2015/0073269 A1* | 3/2015 | Stopek | A61B 5/061 600/424 |
| 2015/0320385 A1* | 11/2015 | Wright | A61B 5/0091 600/474 |

\* cited by examiner

*Primary Examiner* — Hien N Nguyen
(74) *Attorney, Agent, or Firm* — Gazdzinski & Associates, PC

(57) ABSTRACT

This invention provides a non-invasive diagnosis system that is not only capable of producing high-resolution, three-dimensional images of abnormalities of tissue growth inside the body but, it can also detect the type of abnormalities and their location using multispectral imaging techniques. It is possible to provide a portable, non-invasive device that is handheld and with which women may use to screen themselves for early detection of breast cancer without the need to visit a physician. As the present invention uses broadband sources and/or multiple coherent sources, secondary factors such as oxygen metabolism or blood volume associated with the cancer tissues could also be detected to provide further verification of the type. This invention would raise the accuracy of diagnosis and reduce the rate of false positives and false negatives.

19 Claims, 53 Drawing Sheets

Cross-sectional view of contact embodiment (1) AFTER contact and adaptation of breast shape

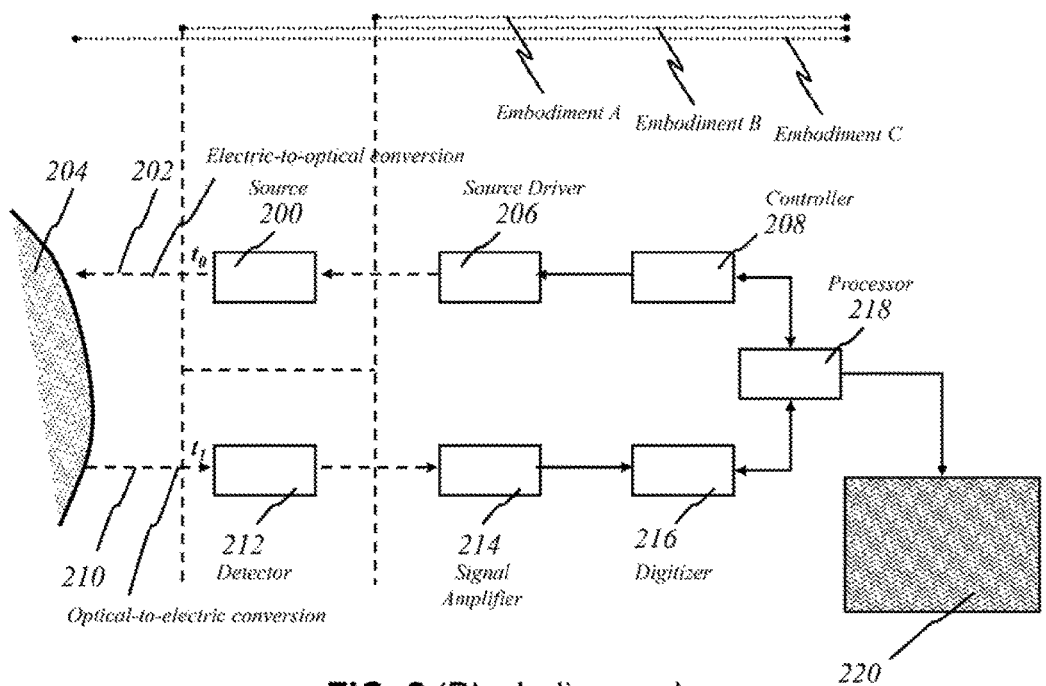
FIG. 2 (Block diagram)

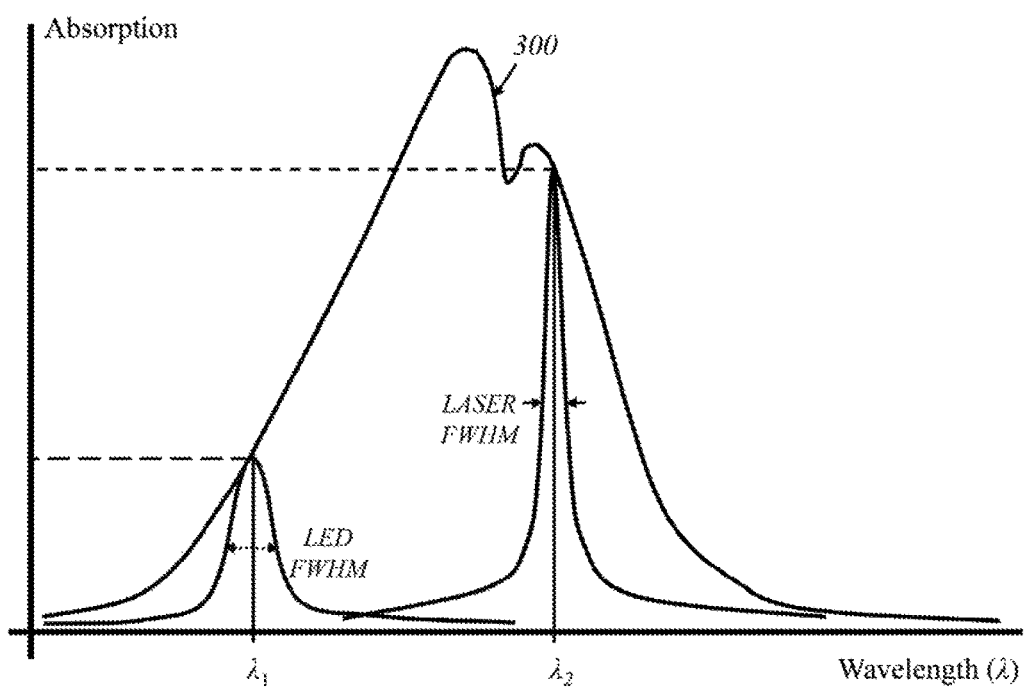
FIG. 3 sample absorption spectrum

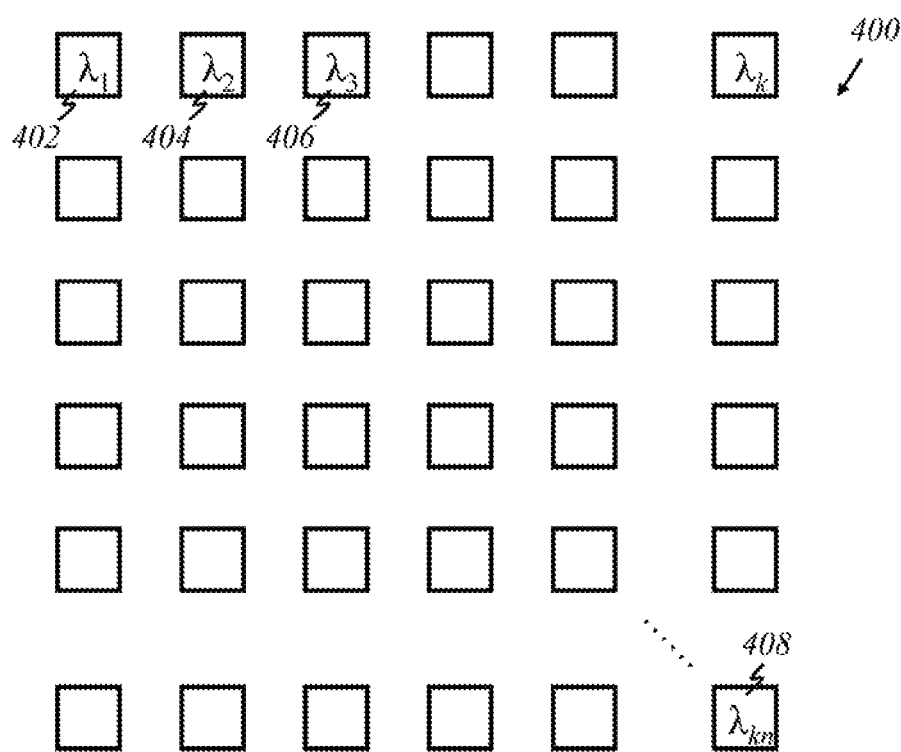
FIG. 4A Sources

Sources

Sources

Sources

Sources

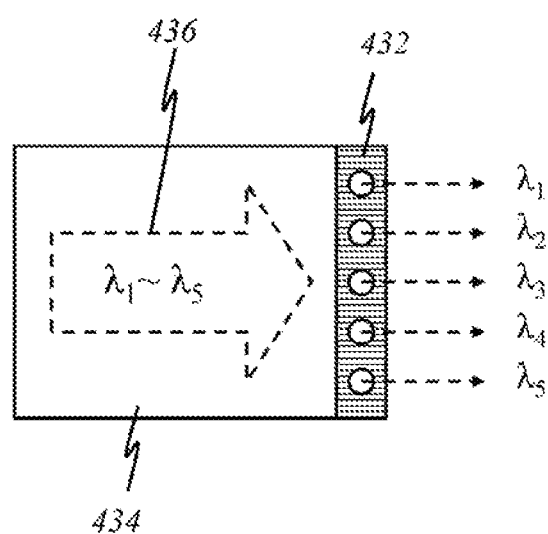
FIG. 4F Source w/ filter

Sources

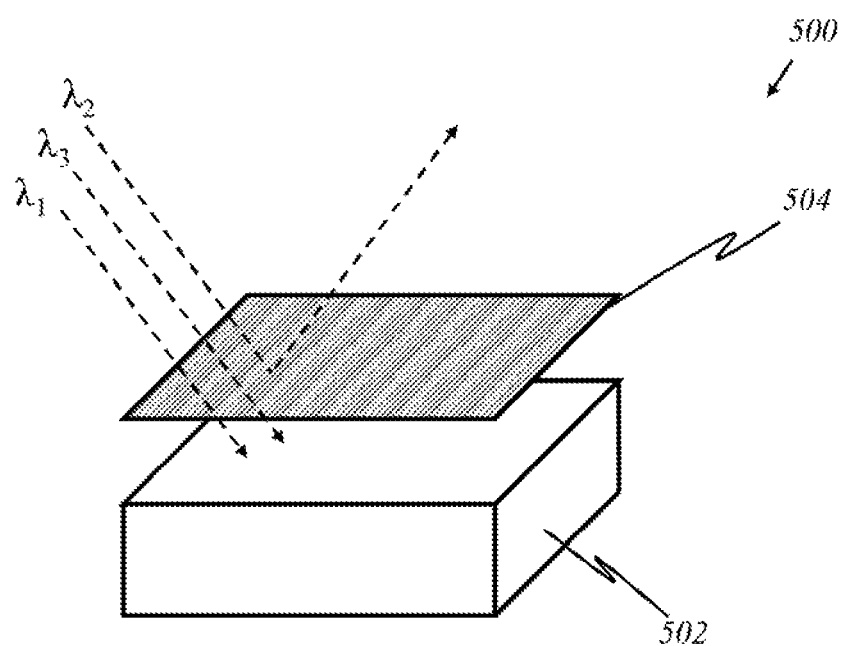
FIG. 5A Detector

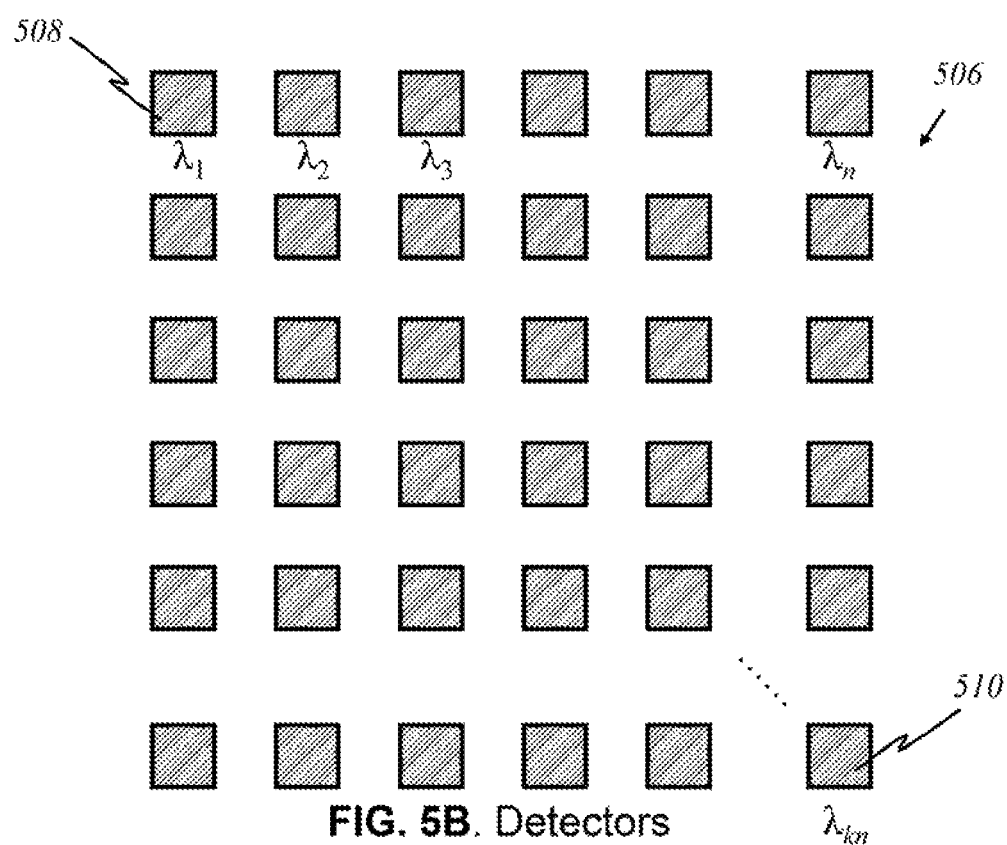
FIG. 5B. Detectors

Detectors

Source + detector

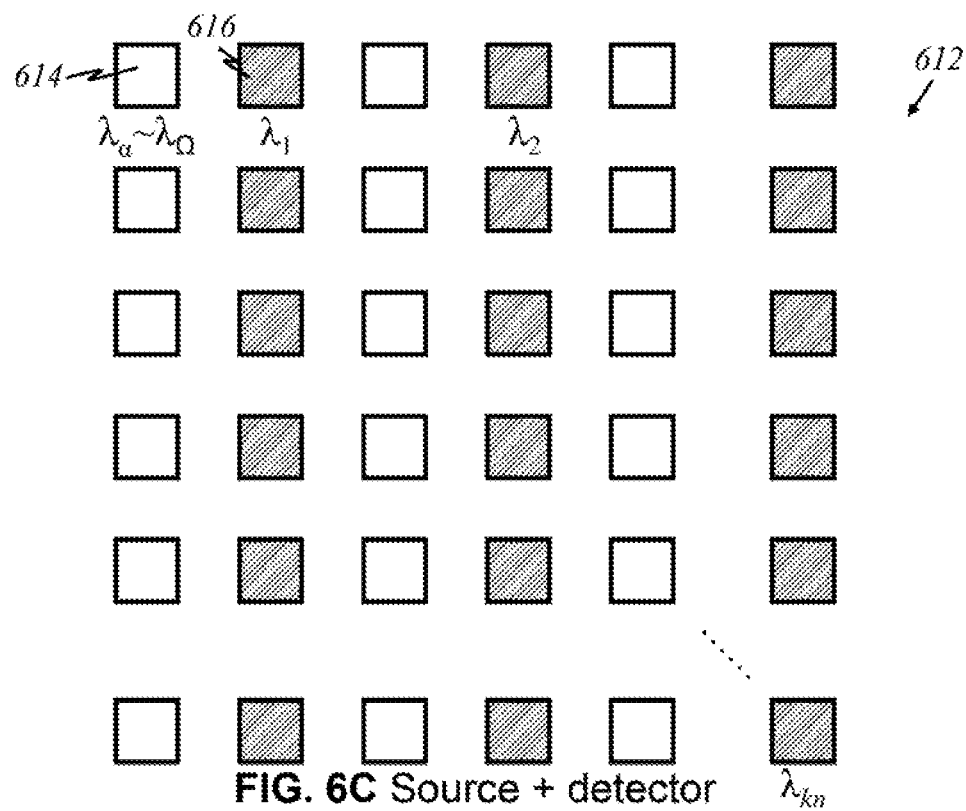
FIG. 6C Source + detector

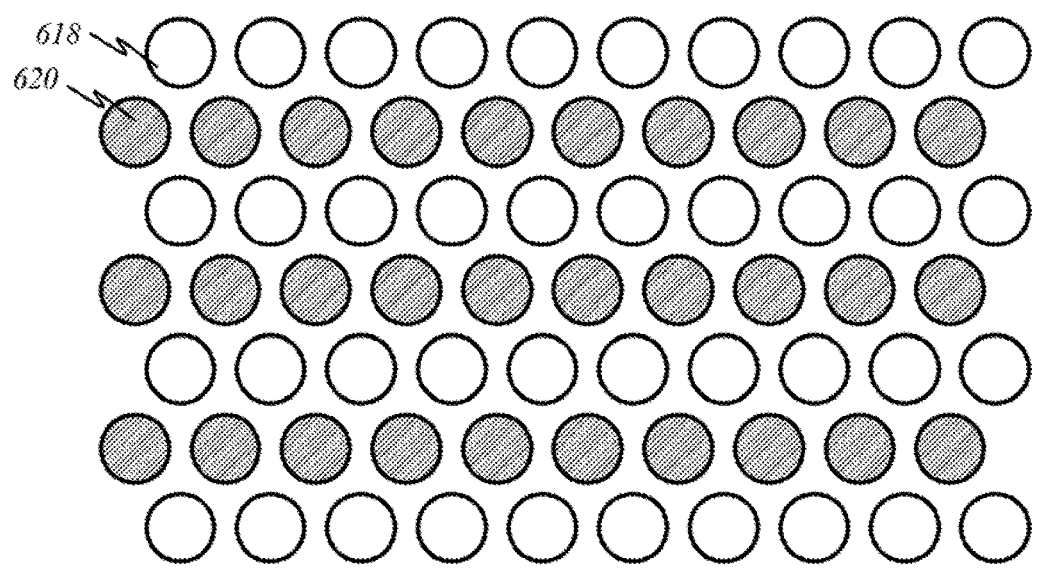
FIG. 6D Source + detector

Angled view of non-contact embodiment (2) optical

Angled view of non-contact embodiment (2) elec

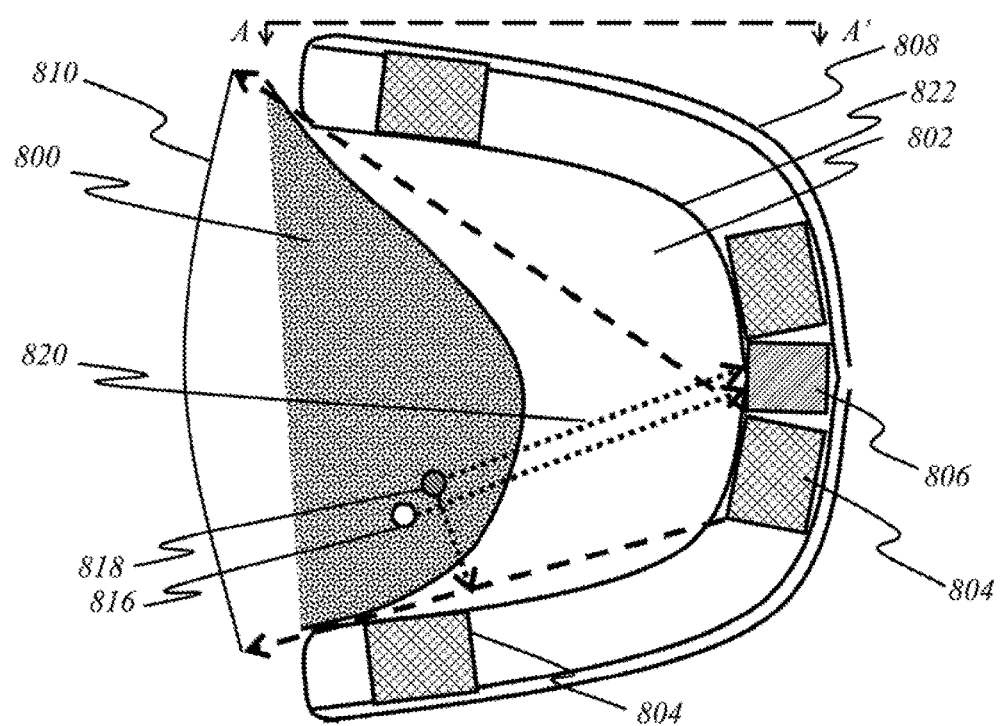
FIG. 8A Cross-sectional view of non-contact embodiment (1)

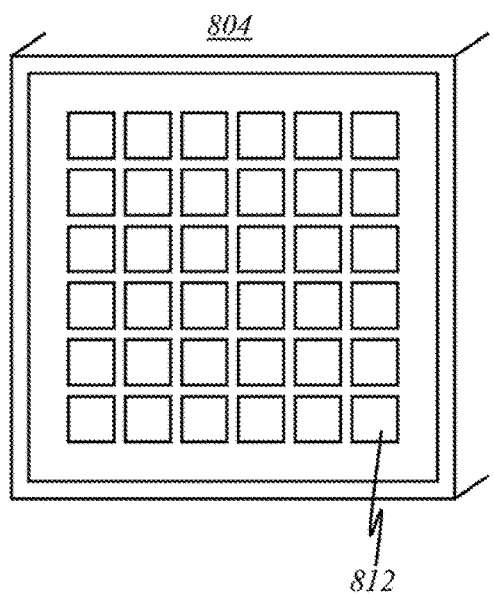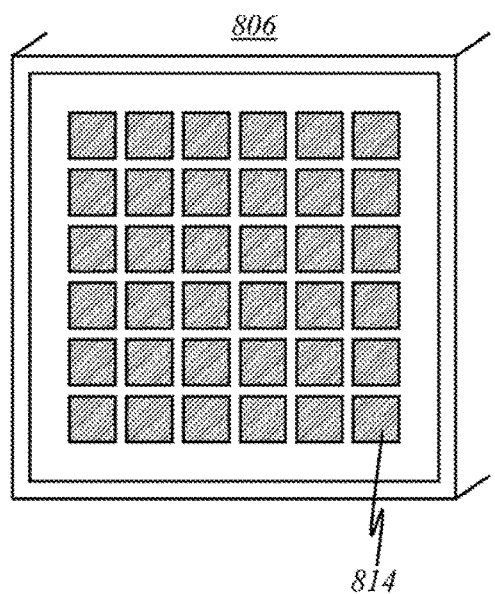
FIG. 8B     FIG. 8C

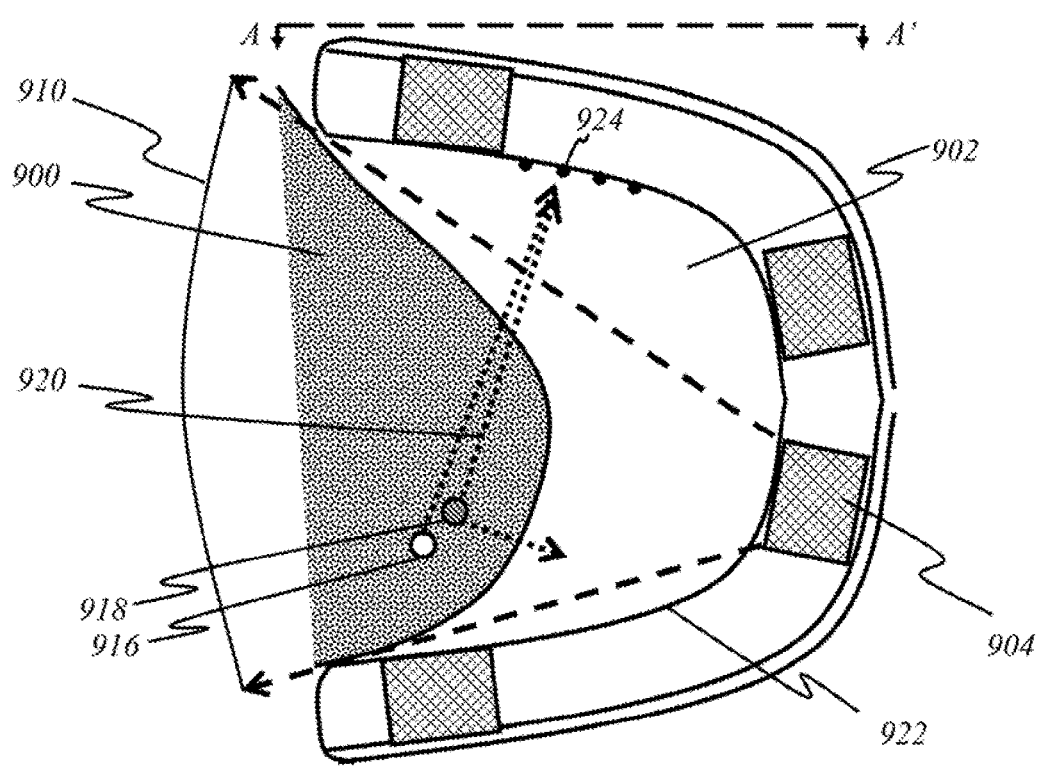
FIG. 9 Cross-sectional view of non-contact embodiment (2)

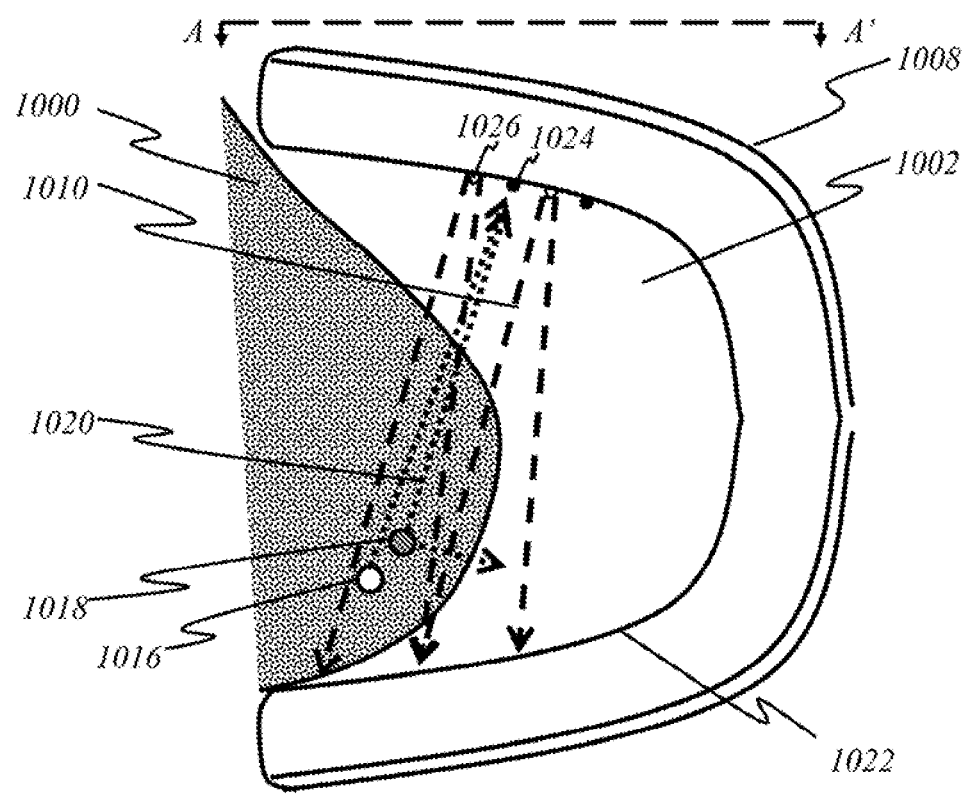
FIG. 10 Cross-sectional view of non-contact embodiment (3)

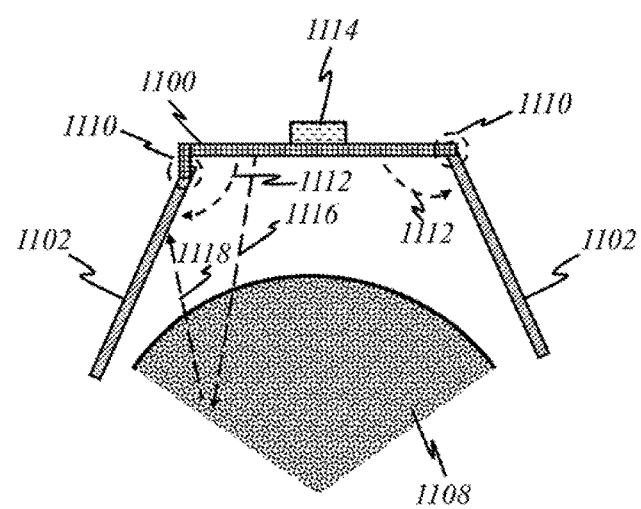
FIG. 11A Cross-sectional top view of non-contact, flip-open embodiment

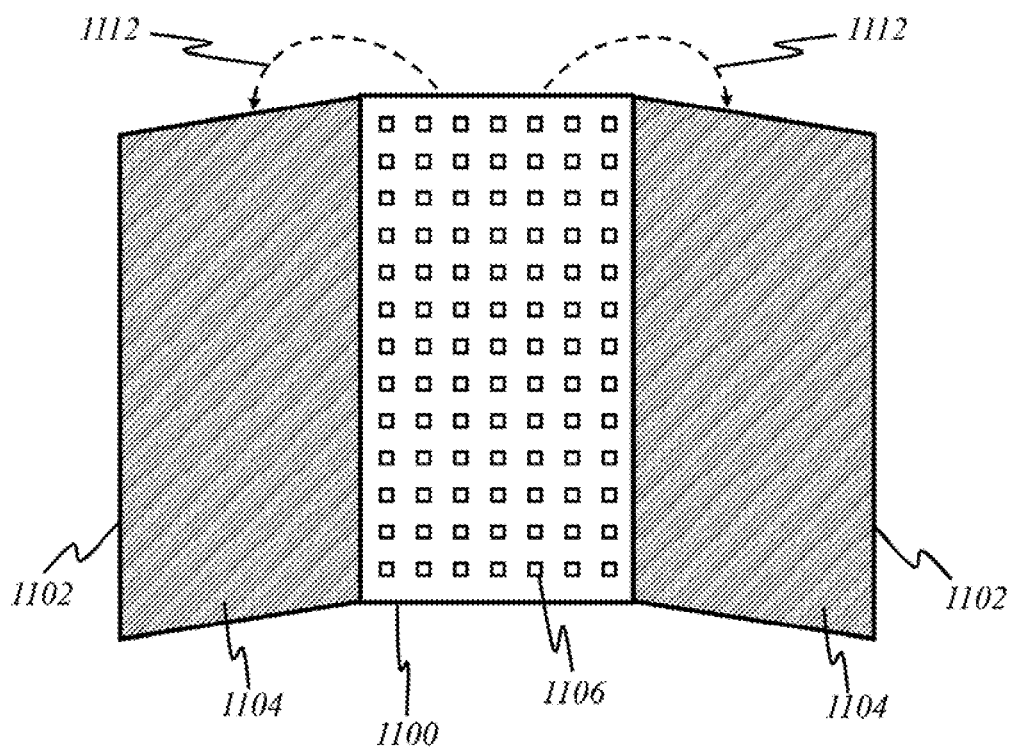
FIG. 11B. Front view of flip-open embodiment (1)

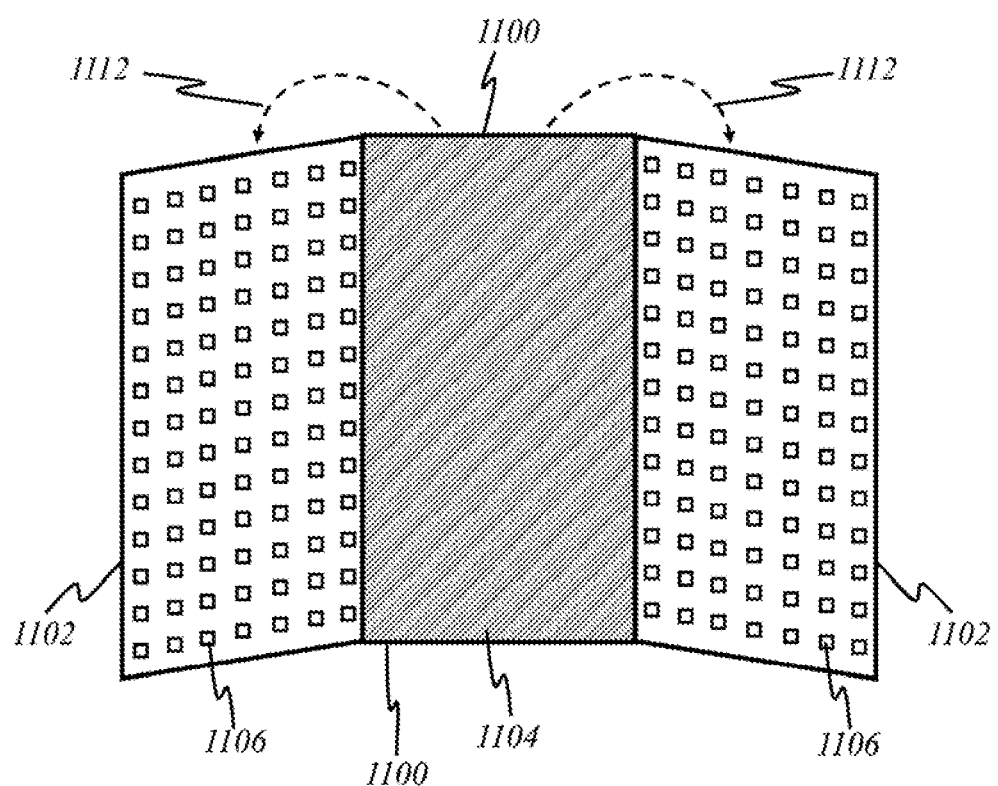
FIG. 11C *Front view of flip-open embodiment (2)*

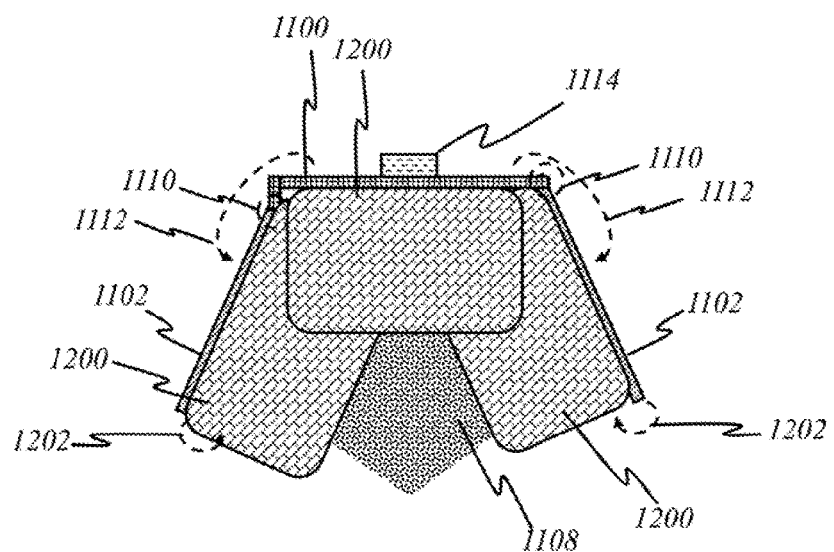
FIG. 12A Top view of non-contact, flip-open embodiment (with shields)

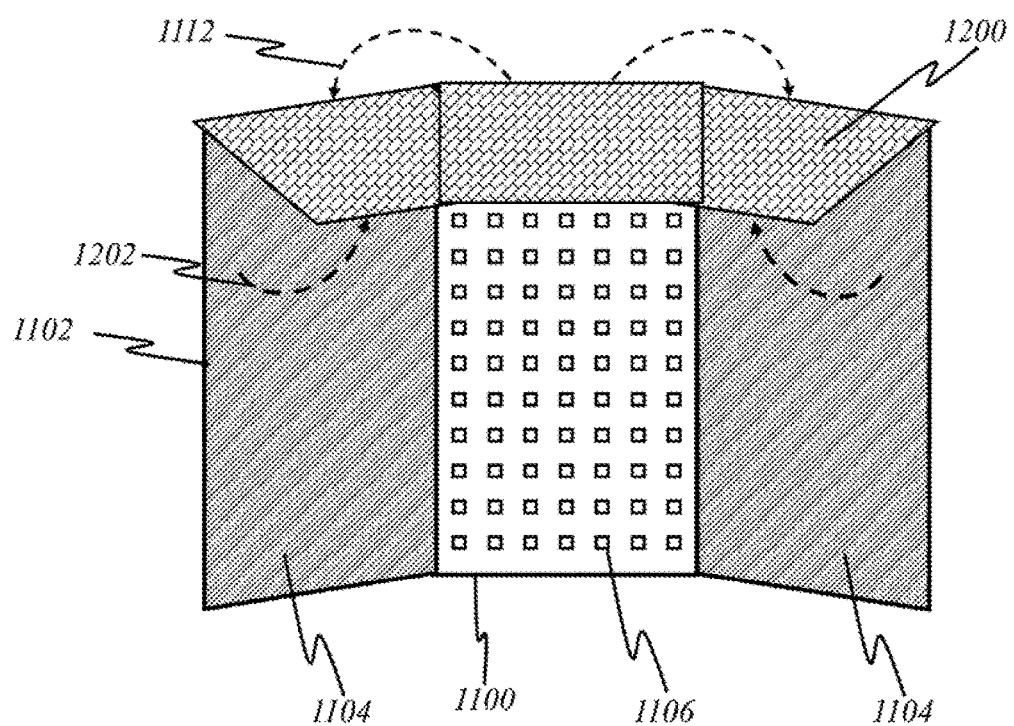
FIG. 12B Front view of flip-open embodiment (1) (with shields)

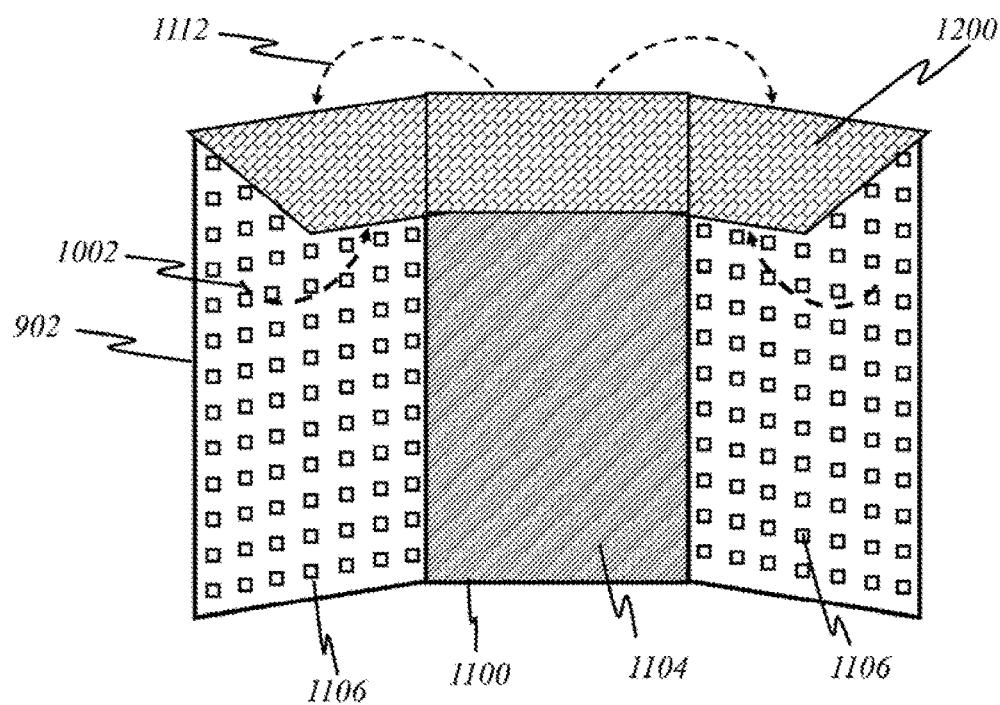
FIG. 12C Front view of flip-open embodiment (2) (with shields)

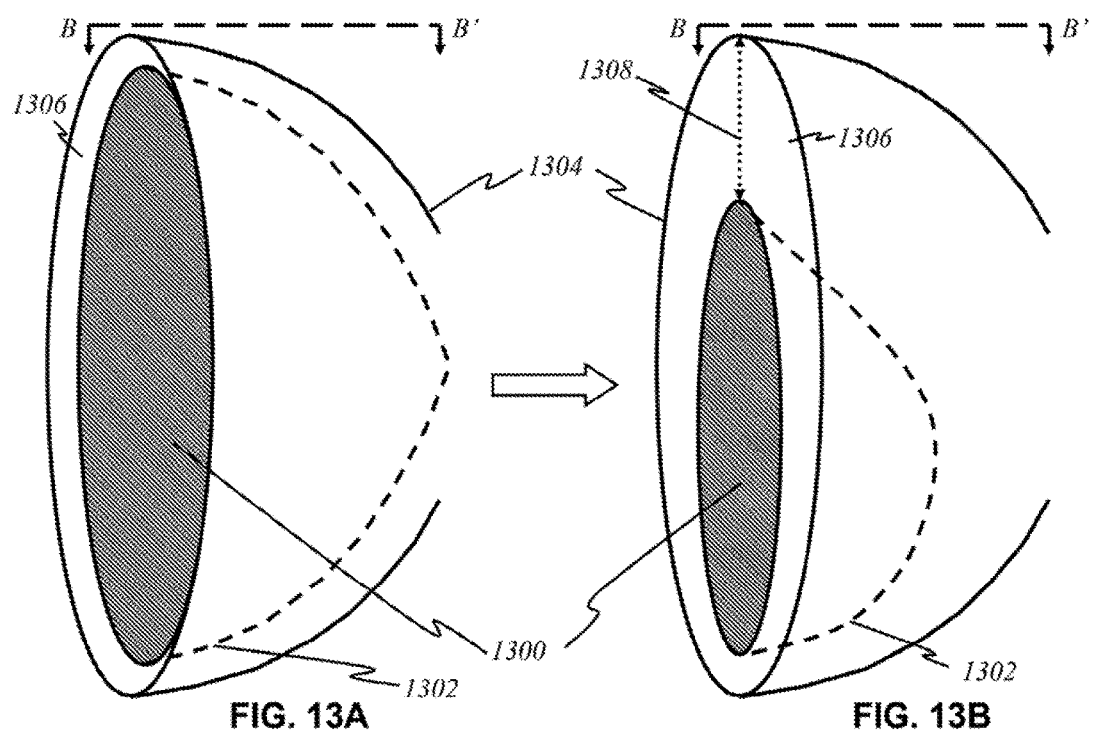
Angled view of self-adjusting cavity

Contact – self-adjusting cavity, cross section

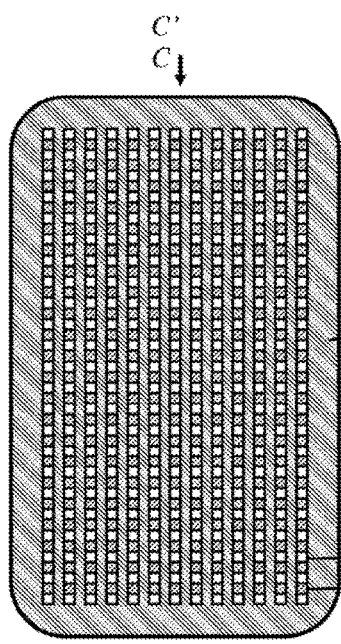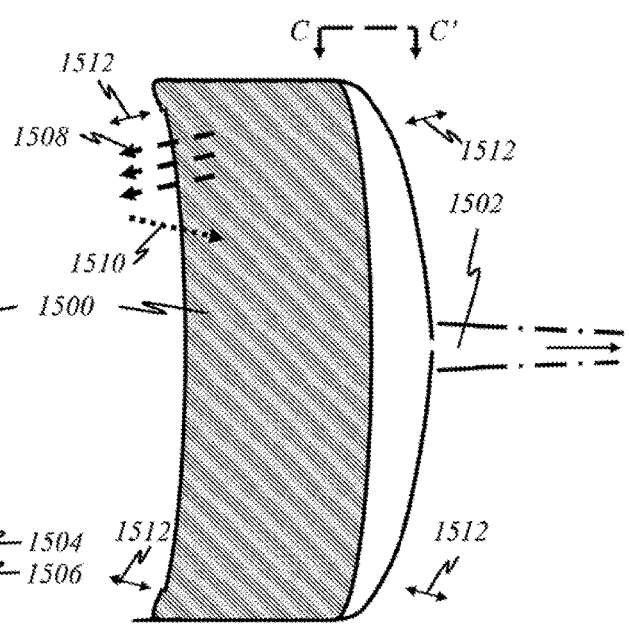
FIG. 15A    FIG. 15B
Front & angled view of flat contact embodiment BEFORE contact

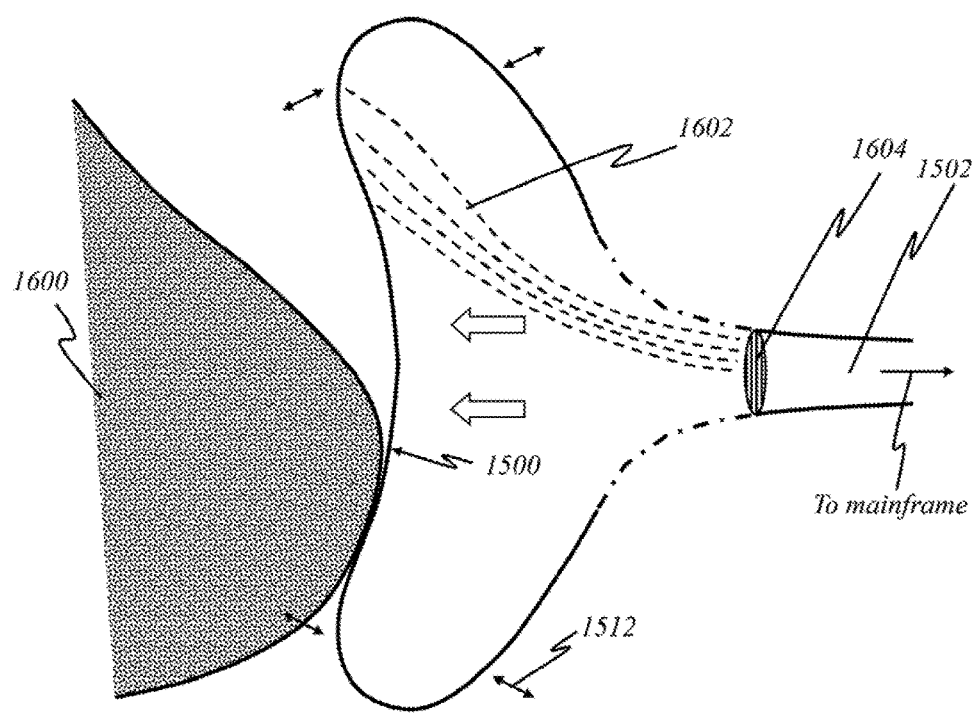
FIG. 16A Cross-sectional view of contact embodiment BEFORE contact and adaptation of breast shape Cross-sectional view of contact embodiment BEFORE contact and adaptation of breast shape (elec)

separate figure showing enlarged view of 1220 and 1224

Cross-sectional view of contact embodiment (1) AFTER contact and adaptation of breast shape

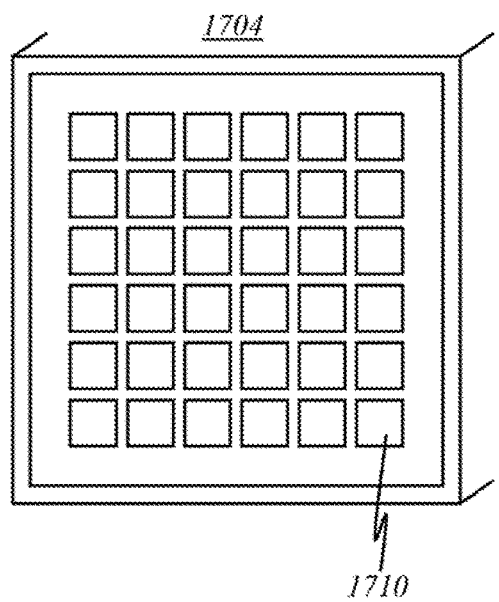 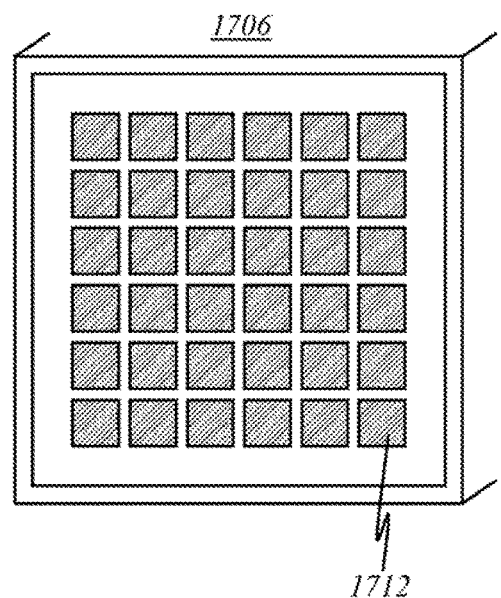
FIG. 17B  FIG. 17C

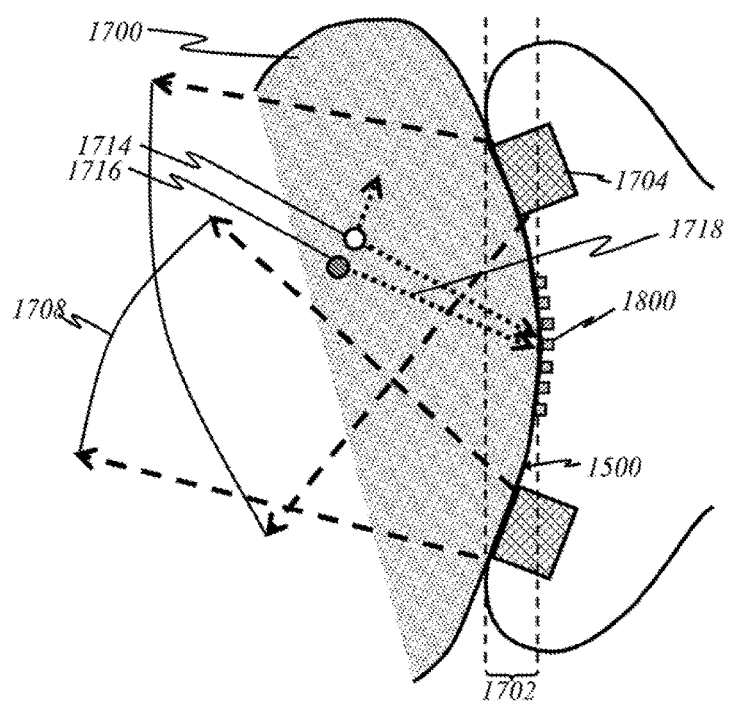
FIG. 18 Cross-sectional view of contact embodiment (2) AFTER contact and adaptation of breast shape Cross-sectional view of contact embodiment (3) AFTER contact and adaptation of breast shape

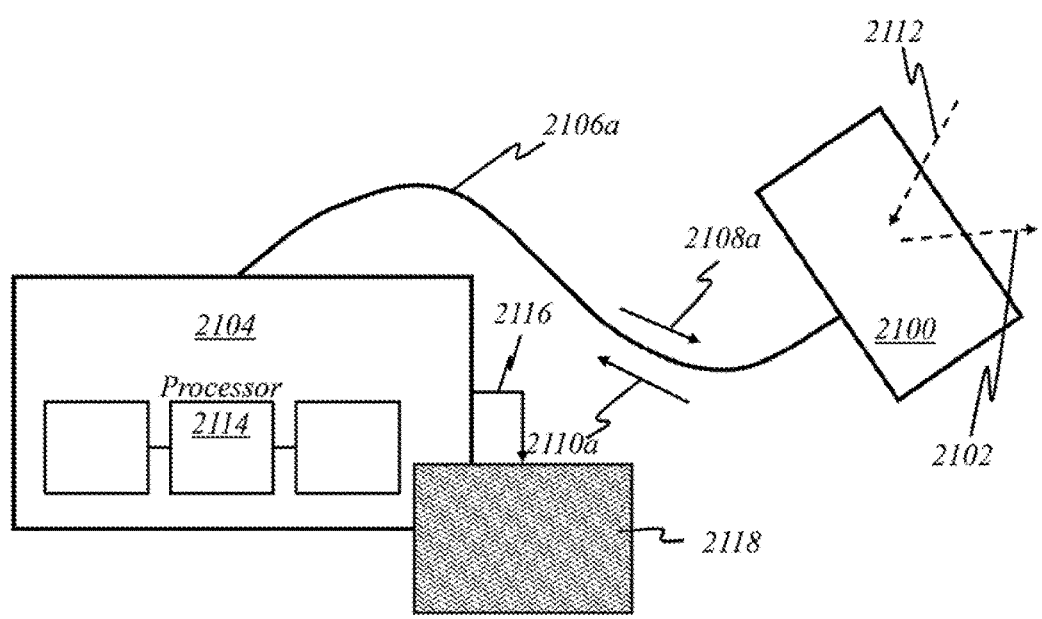
FIG. 21 Whole view (general schematic diagram)

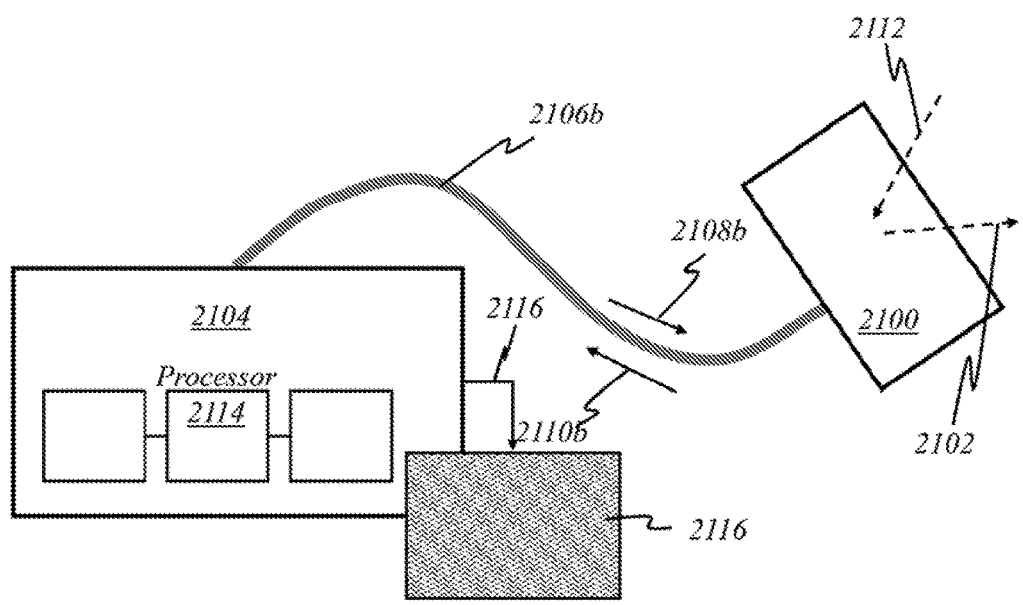
FIG. 22 Whole view (with electrical wire)

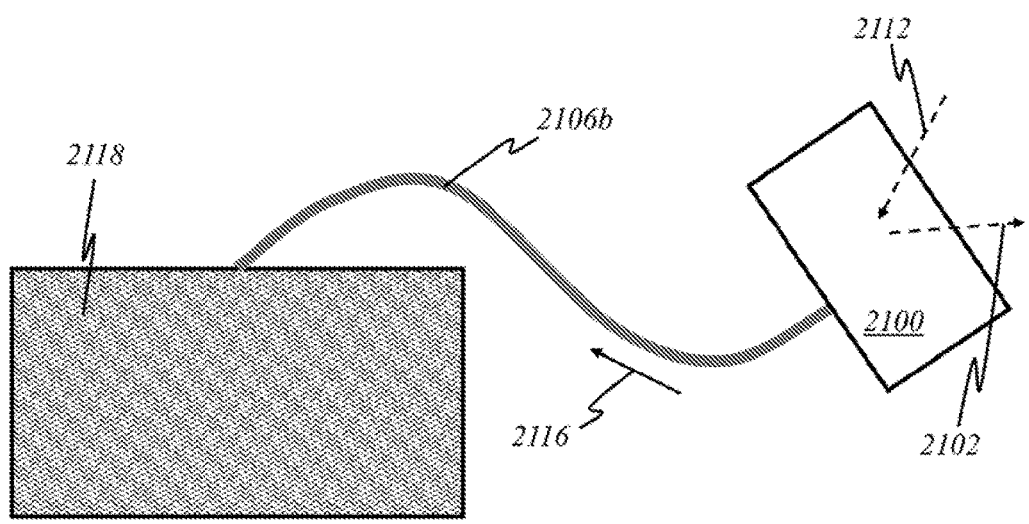
FIG. 23 Whole view (2) (with electrical wire)

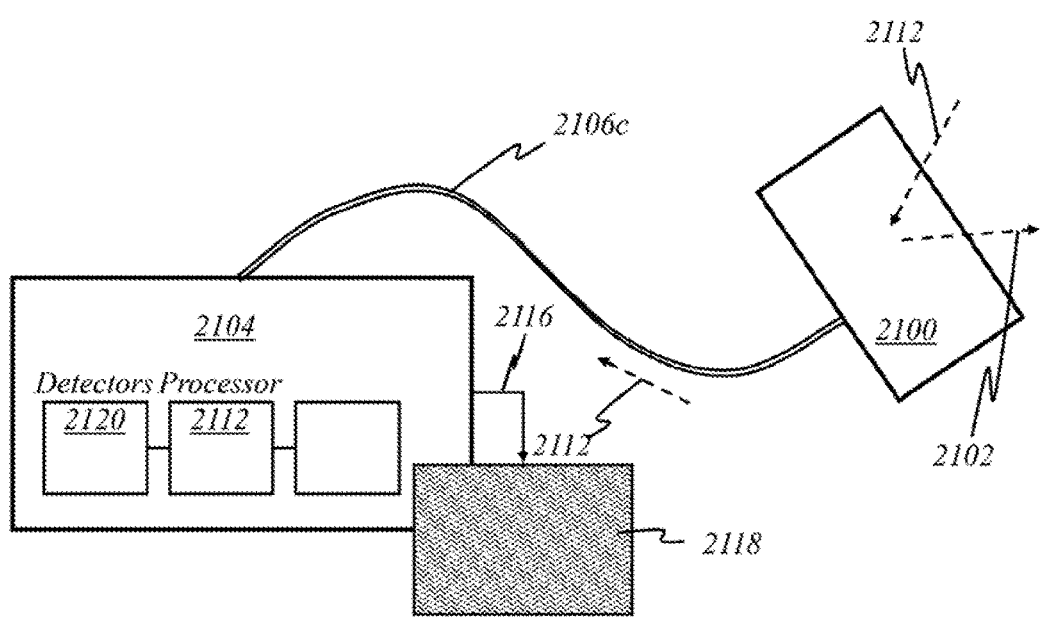
FIG. 24 Whole view (with optical fiber) (1)

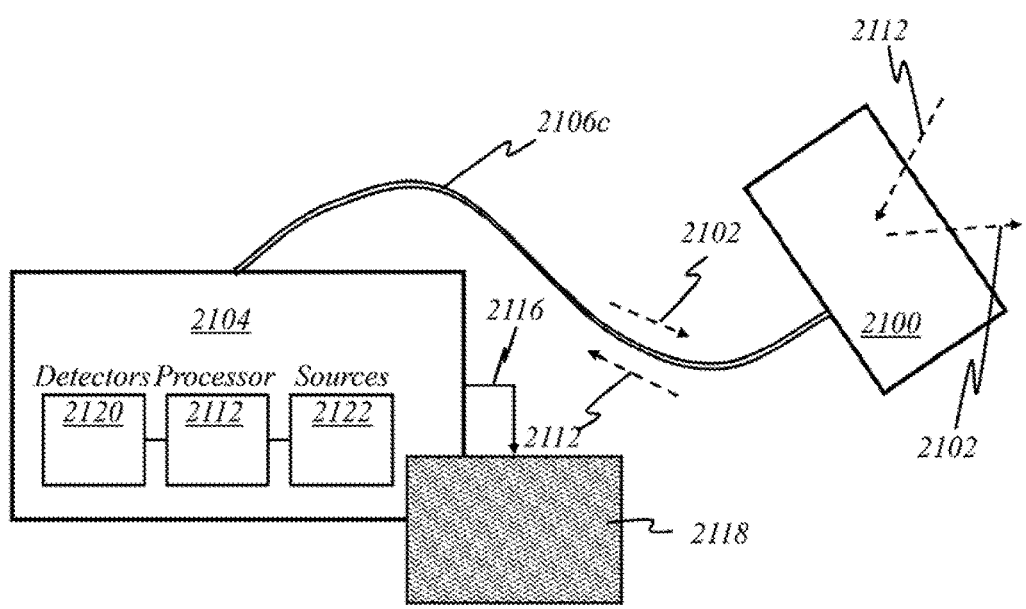
FIG. 25 Whole view (with optical fiber) (2)

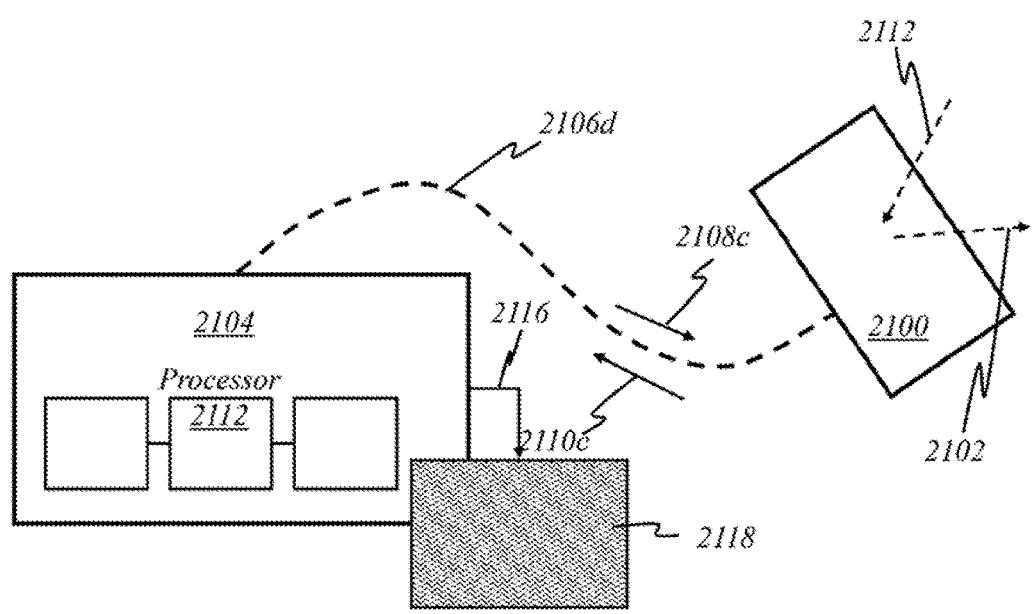
FIG. 26 Whole view (without wire)

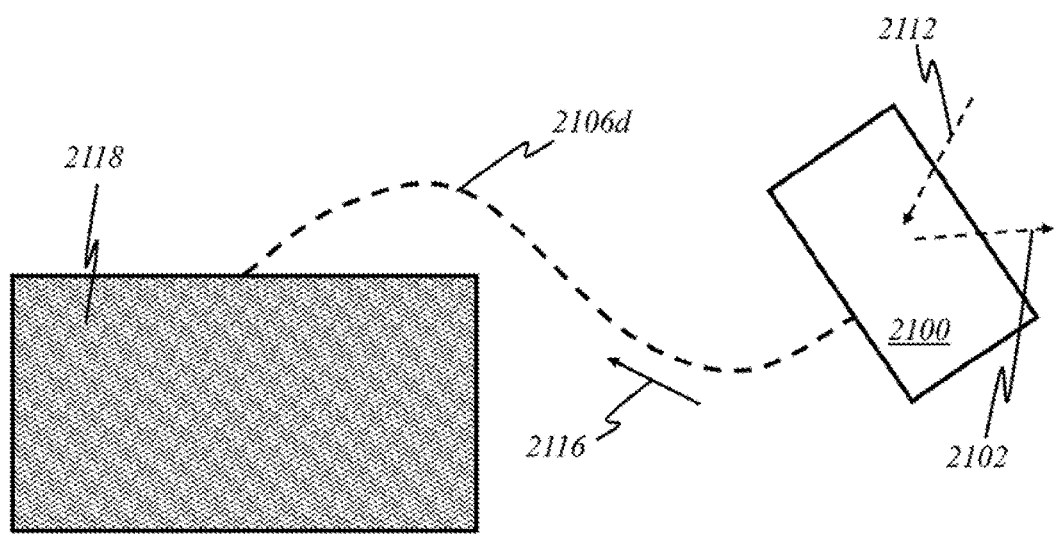
FIG. 27 Whole view (2) (without wire)

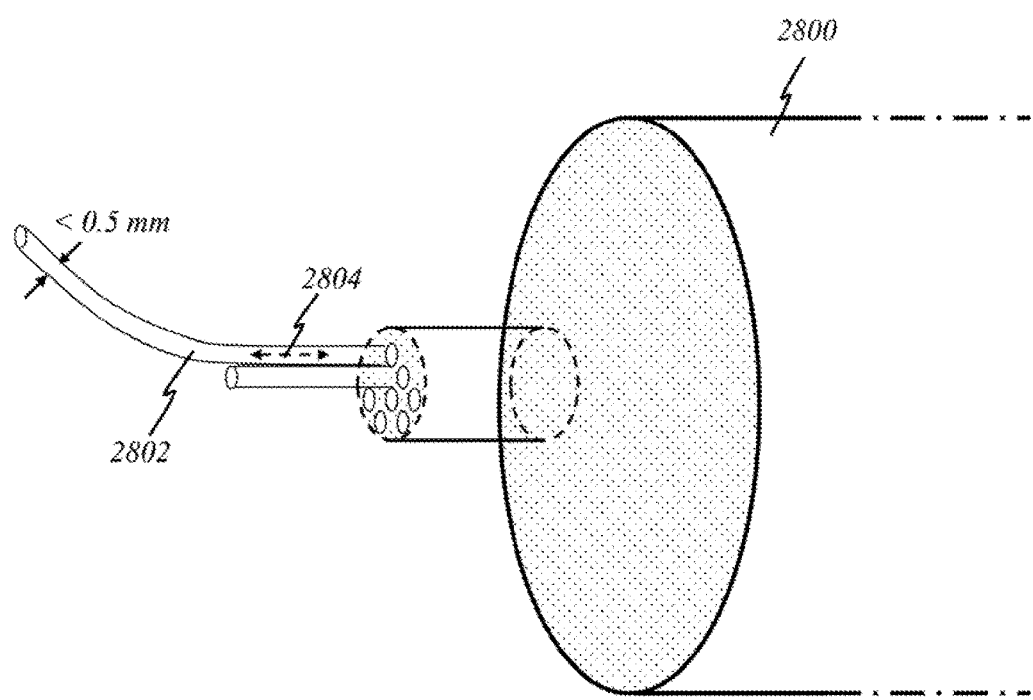
FIG. 28 Optical-fiber cable

Device shapes (a)

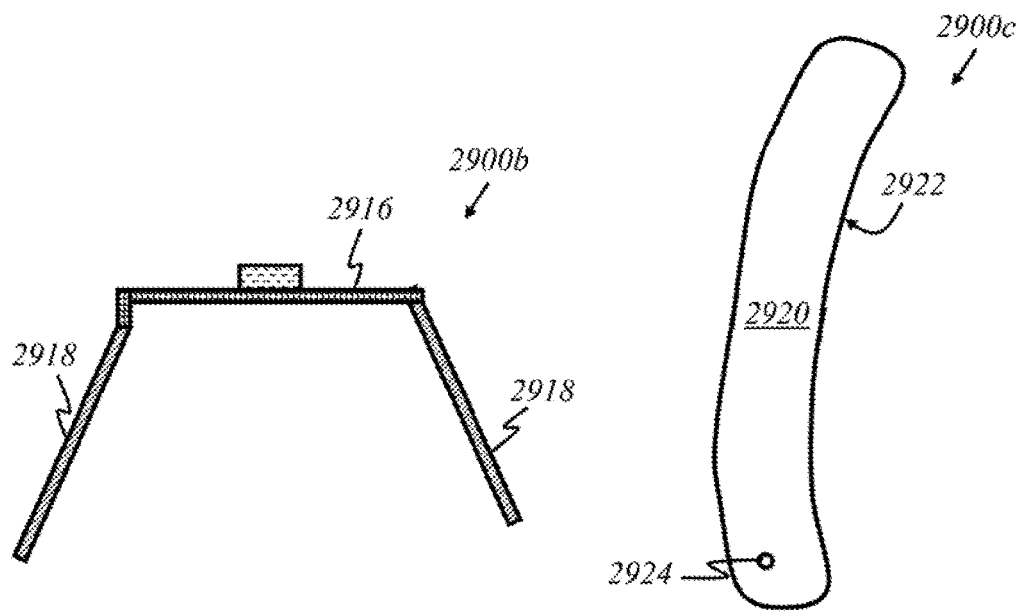

IMAGING SYSTEM FOR SCREENING AND DIAGNOSIS OF BREAST CANCER

FIELD OF THE INVENTION

This invention relates to detection of subcutaneous cellular mass utilizing optics and imaging techniques. More particularly, this invention is related to detecting (a) abnormal growth of tissues inside the body, (b) their types, (c) their dimensions, and (d) their location from outside the body (through non-invasive contact or non-contact with the body). More specifically, this invention is related to the means to detect abnormalities of tissue growth inside the body, their types, dimensions, and location from outside, more particularly the early diagnosis of the cancer, especially breast cancer. This invention also relates to a medical device that emits electromagnetic waves of varying wavelengths and detects waves returned to the device.

BACKGROUND OF THE INVENTION

Breast cancer is an uncontrolled growth of cells in breast tissue caused by a genetic abnormality, resulting in malignant tumors, typically originating from the inner lining of milk ducts, glands that supply the ducts with milk, or less commonly, from the fatty and fibrous tissues.[1] Nearly all cases of breast cancer occur in women.[2] Statistically, breast cancer accounts for the most deaths caused by all other cancers except lung cancer, and about one in eight women who reach the age of eighty will have developed breast cancer.[1] Older women are more at risk of having breast cancer.

In early stages (i.e., stage 0 and stage 1A) of breast cancer, cancer cells stay in the breast. As the cancer progresses, cancer cells eventually spread into the underarm lymph nodes. Lymph nodes are small organs of the immune system located throughout the body, including the armpit, which are linked by vessels. If cancer cells spread into the lymph nodes, they have access to other parts of the body.

Early detection is paramount to preventing breast cancer from progressing to dangerous stages. If detected in its early stages, it is likely that the tumor is small and still confined to the breast and therefore more likely to be treated successfully. However, if the tumor is not detected until it has grown large and spread into the lymphatic system, chances of survival are greatly decreased. Therefore, it is important that women be screened often to catch the cancer early and increase their chances of survival. Unfortunately, there is no device available that a woman may use to regularly screen herself for breast cancer at home. Currently, alternative detection and screening methods exist, including physical examination, genetic screening, mammography, ultrasound-based screening, and breast magnetic resonance imaging (MRI), among others. A clinical or self-performed breast examination involves feeling the breast for abnormalities. It is not an effective preventive method because finding a lump likely indicates that the tumor has already been growing for years. There is no evidence that routine examination reduces morality rates, and it is no longer a recommended screening method.

Genetics play a minor role in determining risk factors. Genetic testing focused on inherited BRCA1 and BRCA2 gene mutations allow women to assess a risk profile for developing breast cancer before a certain age. Such genetic screening does not detect the presence of breast cancer, but it may reveal a person's susceptibility to develop it. The U.S. Preventive Services Task Force, composed of primary care and prevention experts, recommends against routine testing unless family history suggests a higher risk of BRCA1 or BRCA2 mutations. Having a close relative diagnosed with breast cancer increases a woman's risk of breast cancer. However, about eighty-five to ninety percent of breast cancers occur naturally in women who have no family history of breast cancer. Only five to ten percent of occurrences are caused by inherited mutations. Therefore, to detect breast cancer early, it is important to perform regular testing rather than rely on one's susceptibility to breast cancer. Moreover, since only a small percentage of breast cancer occurrences is caused by inheriting mutations, it is not a method that would be beneficial for the general public.

The two leading techniques for breast cancer screening are mammography (see FIG. 1A) and magnetic resonance imaging (MRI). Mammography is a diagnostic and screening procedure whereby low-energy X-rays are used to create images, which are then reviewed by a physician for signs of cancer. The American Cancer Society recommends that women over the age of forty receive a screening mammogram every year. Some studies show that the decrease in rate of breast cancer deaths is due to mammography. However, there is continued debate about whether this method is less helpful than it is helpful. For example, one of the drawbacks is that false positives create long-lasting psychological stress and anxiety, which can affect the patient's wellness and behavior for many years. On the other hand, false negatives estimated up to thirty percent occur, which can lead to missed opportunities for treatment if regular checking is not done. Mammograms do not work well in younger women because their breast tissue is denser. Cost can further be an issue, more so because insurance policies tend not to cover mammograms for women under forty, even though women in their teens or twenties are sometimes diagnosed with breast cancer. Ultimately, it has been shown that death rates over 25 years were the same among women ages 40 to 59 regardless of whether or not they underwent regular mammograms. Other drawbacks include discomfort and limitation in detection accuracy. Patients undergoing mammograms have their breasts compressed, which can cause pain or discomfort. Tumors sized smaller than one millimeter are difficult, if not impossible, to detect. Given the balance of benefits, drawbacks and costs, overtreatment by mammography is common. Medical ultrasonography is a supplement to mammography that uses ultrasound to image breast tissue that is denser or deeper in from the surface of the skin. While it increases the detection rate of breast cancer, it also increases the rate of false positives. Ultimately, even purely ultrasound-based screening may warrant an invasive biopsy procedure to confirm whether a tumor exists in the tissue sample removed from the patient's body and determine whether that tumor is benign (non-cancerous) or active (malignant).

Breast MRI is an alternative to mammography. Breast MRI may also be recommended to accompany mammography in women at high risk for breast cancer. In MRI, magnets and radio waves are used to create pictures of the breast and surrounding tissue. Its main benefit over mammography is that it dramatically reduces false negatives, giving a negative result great certainty in ruling out the presence of cancer. Breast MRI is more sensitive and able to detect the presence of cancer cells that are not detectable via mammograms, including tumors that are too small, tumors within dense tissue material, and tumors that are clearly benign. However, it also produces greater false positives and is expensive, costing thousands of dollars. It requires a specialist to administer the MRI and interpret the results. It is a time-consuming and invasive procedure requiring injection of a contrast agent that poses a risk to patients with a history of renal disease. Patients with metallic substances inside them, such as a pacemaker or breast reconstruction material, also may not use MRI. Thus, MRI is reserved for certain types of patients, such as those with family history of breast cancer, those who are at genetic risk, or those who have dense or abnormal breast tissue (e.g., implants, scars, augmentations).

Both mammography and breast MRI procedures require a biopsy (see FIG. 1B) to histopathologically verify the presence of cancerous tissue, because not all breast tumors are cancerous and in need of removal. During a biopsy, a physician takes a sample of tissue from the suspicious area of the breast and tests it for cancer. Up to seventy-five percent of biopsies performed on tissue determined to be cancerous by mammogram and MRI have been found to be benign. Removing tissue from the breast can be a physically and psychologically challenging procedure. There exists a need for a screening technique that eliminates the cost and stress of unneeded biopsies.

Recently, there have been attempts to screen for breast cancer without the need for a biopsy. One such method is the use of computer-aided tomography (CAT scans) for breast cancer imaging. A dye is introduced intravenously and two-dimensional cross sectional images of the breast are produced. A computer may then combine these images to produce detailed pictures. Currently, this technique is not used for breast cancer screening and is typically only used for large-scale imaging of the entire body to determine if the cancer has spread from the breast area. In addition, this technique is not non-invasive because it requires the injection of the dye as well as a visit to the physician. Similar to the use of CAT scans is the use of fluorescent probes and near-infrared radiation (NIR). To use fluorescent probes, a drug is introduced to the test subject intravenously that will preferentially absorb into cancerous cells. It then interacts with the cells in vivo to produce a dye whose fluorescence may be imaged when exposed to a particular wavelength of light. While the use of light in the NIR range has the advantage of being highly sensitive and specific (can also reach deep tissue), it has the same problems as CAT scans in that it requires the injection of a drug and cannot be performed without the aid of a physician.

NIR can be used in a less-invasive technique that studies oxygen metabolism and blood volume in tissue. Since tumors grow more rapidly and require more nutrients than normal tissue, tumors also require additional blood vessels to supply these nutrients. Detecting the presence of additional blood volume and changes in blood oxygenation can thus be indicative of a tumor. Through NIR imaging, areas of large hemoglobin density (i.e., cancerous tissue) may be evidenced by areas of shadow when illuminated by NIR light at certain wavelengths because hemoglobin absorbs light at these wavelengths. This technology has the advantage of being non-invasive and capable of use as a home diagnostic device. However, this technology is limited by the difficulty in distinguishing between absorption and scattering in tissue, as well as the need to rely on secondary factors (oxygen metabolism and blood volume) to determine the presence of a tumor.

Breast cancer screening remains an important procedure for women because of breast cancer's implications to their psyche, their body and their very life. Breast cancer has been known for thousands of years, and modern medical successes have allayed confusion from times past and provided ways to potentially save women's lives. Nevertheless, it can be seen that current methods of breast cancer screening and diagnostic methods can be stress inducing, unreliable, bulky, invasive, and costly. Moreover, some women may also feel a stigma associated with breast cancer, and going through medical procedures related to breast cancer can make them feel especially vulnerable to privacy issues.

Therefore, it would be useful and desirable to have a portable, non-invasive device that is handheld and with which women may use to screen themselves for breast cancer without the need to visit a physician. The present invention provides such a non-invasive device that is not only capable of producing high-resolution, three-dimensional images of abnormalities of breast tissue but it can also detect the type of abnormalities and their location using multispectral imaging techniques. As the present invention uses broadband sources and/or multiple coherent sources, secondary factors such as oxygen metabolism or blood volume associated with the cancer tissues could also be detected to provide further verification of the type. Quick delivery of images and results in the privacy of one's home allows the user to interpret the results and decide whether to invest further time and energy by visiting a physician.

SUMMARY OF INVENTION

The present invention aims to overcome problems associated with current technologies by providing a device that is friendly to users and makes screening and diagnosis of breast cancer more sensitive, more rapid, non-invasive, and less costly, allowing for early detection of emerging tumors through routine self-examination.

The following presents a summary of the invention and a basic understanding of some of the aspects of the invention. It is not intended to limit the scope of the invention or provide critical elements of the invention. Its sole purpose is to present some of the features of the invention in a simplified form as a prologue to the more detailed description presented later.

In one aspect of the present disclosure, an imaging system is disclosed. In one embodiment thereof, the imaging system is for detection of breast cancer, and the system includes a handheld device that includes an interface configured to make direct contact with biomass; and a non-transitory computer-readable apparatus including a storage medium having at least one computer program, the at least one computer program including a plurality of instructions configured to, when executed by a processor apparatus, cause the processor apparatus to, when the handheld device makes direct contact with the biomass via a surface of the interface, cause a source of the handheld device to emit a broadband signal including a plurality of wavelengths; based on a returning signal detected from the biomass, determine a position of a given volume of tissue within the biomass, the detected signal being associated with a wavelength from the plurality of wavelengths of the emitted broadband signal; and determine a size of the given volume of tissue based on the wavelength associated with the detected signal.

In another aspect of the present disclosure, an imaging device is disclosed. In one embodiment thereof, the imaging device is a handheld imaging device for detection of breast cancer, and the device includes a receptacle that includes a cavity configured to receive biomass, the biomass including a volume of tissue of interest, and the receptacle includes: one or more light sources configured to emit a broadband signal including a plurality of wavelengths toward the cavity; and one or more photodetectors configured to detect a returning signal from the cavity; and a non-transitory computer-readable apparatus including a storage medium having a software program, the software program having instructions configured to, when executed by a processor apparatus, cause the device to emit the broadband signal toward the biomass when the cavity contains the biomass; and when the returning signal is detected, (i) detect a depth and a size of the volume of tissue of interest within the biomass based on the wavelength associated with the returning signal, and (ii) determine a potential malignancy of the volume of tissue of interest.

In another aspect of the present disclosure, a non-transitory computer-readable apparatus is disclosed. In one embodiment thereof, the non-transitory computer-readable apparatus has a computer program, the computer program including a plurality of instructions configured to, when executed by a processor apparatus, cause the processor apparatus to: cause an emission of a first broadband signal comprising a plurality of wavelengths toward a biomass, the biomass comprising a target volume of tissue; and when a returning signal is detected from the target volume of tissue, the returning signal comprising a wavelength from the plurality of wavelengths: determine a size of the target volume of tissue based on the wavelength of the returning signal; compare one or more optical parameters of the returning signal to one or more known optical parameters associated with malignant tissue; and determine a malignance of the target volume of tissue based on the comparison of the optical parameters.

It is an object of this invention to allow breast cancer screening and diagnosis to be non-invasive.

It is an object of this invention to encourage routine breast cancer screening that is self-operable, more private, easier to use, yet cost-effective.

It is an object of this invention to raise the accuracy of diagnosis and reduce the rate of false positives and false negatives.

It is an object of this invention to incorporate several cancer-detecting techniques to achieve high accuracy.

BRIEF DESCRIPTION OF DRAWINGS

For a better understanding of the aforementioned aspects of the invention and additional aspects and embodiments thereof, reference should be made to the Detailed Description, below, in which reference numerals refer to corresponding parts throughout the figures under Drawings.

FIG. 2 shows a block diagram illustrating the basic operational parts of the present invention.

FIG. 3 shows a sample graph of an example of an absorption spectrum.

FIGS. 4A-4G show various arrangements of light sources that may be implemented in accordance to the present invention.

FIG. 5A shows a schematic of basic parts of a light detector.

FIGS. 5B and 5C show various arrangements of detectors that may be implemented in accordance with the present invention FIGS. 6A-6E show various arrangements of sources and detectors that may be implemented in accordance to the present invention.

FIG. 8A shows a schematic of the preferred "non-contact" embodiment in a cross-sectional view.

FIGS. 8B and 8C show schematics of a source panel and a detector panel, respectively, used in the preferred "non-contact" embodiment.

FIG. 9 shows a schematic of another preferred "non-contact" embodiment in a cross-sectional view.

FIG. 10 shows a schematic of another preferred "non-contact" embodiment in a cross-sectional view.

FIG. 11A shows a schematic of a preferred "flip-open non-contact" embodiment in a top view.

FIGS. 11B and 11C show schematics of the preferred "flip-open non-contact" embodiment in a front view.

FIG. 12A shows a schematic of another preferred "flip-open non-contact" embodiment in a top view.

FIGS. 12B and 12C show schematics of the another preferred "flip-open non-contact" embodiment in a front view.

FIGS. 13A and 13B show schematics of a preferred embodiment with a self-adjusting cavity.

FIGS. 15A and 15B show schematics of a preferred "flexible contact" embodiment in a front view and an angled view, respectively.

FIGS. 16A and 16B show schematics of preferred "flexible contact" embodiments in a cross-sectional view.

FIGS. 17B and 17C show schematics of a source panel and a detector panel, respectively, used in the preferred "flexible contact" embodiment.

FIG. 18 shows a schematic of another preferred "flexible contact" embodiment in a cross-sectional view after making contact with a breast.

FIGS. 21-27 show a whole view of schematics of operational parts implemented in preferred embodiments of the present invention.

FIG. 28 shows a schematic of an optical-fiber cable used in the present invention.

FIGS. 29A-29C show schematics of the present invention implemented in various example devices.

DETAILED DESCRIPTION OF THE INVENTION

Figure 1A:
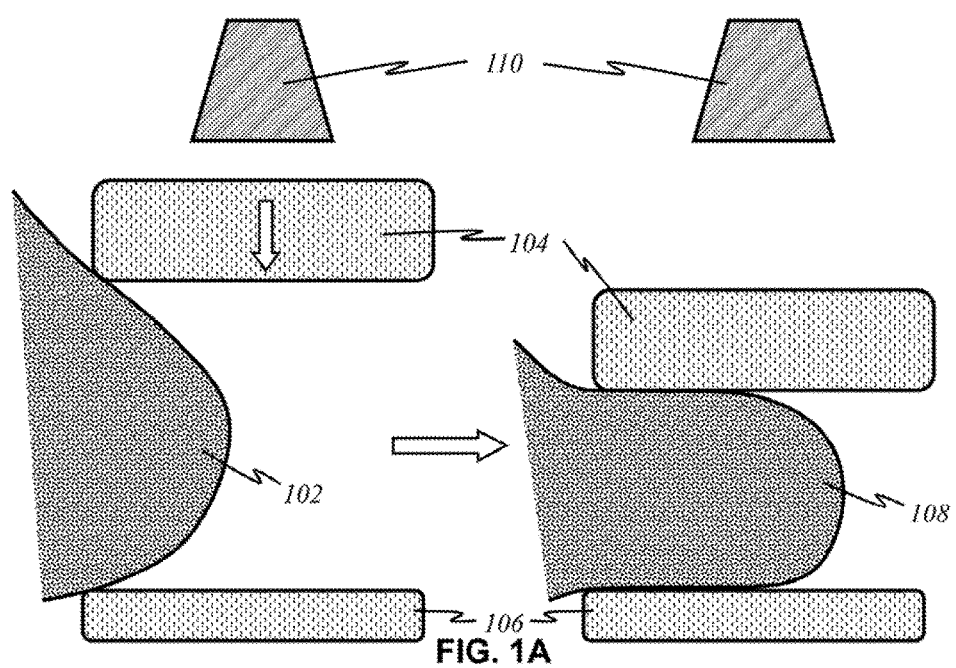
FIG. 1A shows a basic overview of the prior art of mammography.

Reference numerals refer to corresponding parts labeled throughout the figures. The embodiments described herein pertain to a device that detects and images subcutaneous cellular mass through optical techniques. The embodiments pertain to methods and apparatuses for screening and diagnosis of breast cancer.

As used herein, the term "area of interest" and "area of concern" refer to parts of bodily tissue where cancer cells are suspected or known to be. For example, a woman (or man) may undergo mammography on her breasts where she felt a lump. The general area where the lump was would be an area of concern because it is suspected that cancer cells may be developing in the lump. In particular, a "tumor" is an abnormal growth of cells, especially malignant neoplasms that invade nearby cells (cancer).

As used herein, the term "biomass" refers to a total mass or volume of organic matter, typically from the human body. It could be an entire organ or portion thereof, a section of skin, lymph or blood vessels present throughout the body, and/or a collection of cells, ex vivo or in vivo. In the present invention, discussion of "biomass" is aimed primarily at the breast as well as internal and external components of the breast up to the chest cavity.

As used herein, the terms "light," "radiation," "electromagnetic wave" and "electromagnetic waves" are interchangeable, unless specified. "Broadband" light refers to light carrying waves of varying wavelengths, typically a range of wavelengths (or a band). Broadband light is generated by a broadband source, which may emit multiple ranges of wavelengths to selectively emit multiple groups of wavelengths. On the other hand, "uniband" or "coherent" light refers to light having one particular wavelength or a narrow range of wavelengths.

As used herein, the terms "reflect," "refract," "scatter," "diffract" and "fluoresce" refer to the behavior of light waves upon interacting with another material. "Reflect" refers to a process in which light and other electromagnetic radiation are cast back after impinging on a surface. "Total internal reflection" occurs when light strikes a medium boundary at an angle larger than a particular critical angle with respect to the normal to the surface. "Refract" refers to change in direction of electromagnetic radiation in passing from one medium to another. The optical density of a medium is the refractive index, an inherent value of the medium. "Fluoresce" refers to exhibiting fluorescence, which is refers to emission of electromagnetic radiation stimulated in a substance by the absorption of incident radiation. "Diffract" refers to exhibiting diffraction, which refers to a deviation in the direction of a wave at the edge of an obstacle in its path. "Scatter" and "diffract" are interchangeable.

As used herein, the term "panel" associated with light sources and light detectors refer to a continuous and generally transparent surface that emits or receives light. Multiple light source and light detector units are housed under a panel. This is distinguishable from a mere collection or array of sources or detectors. An array is an arrangement of sources or detectors, but each source or detector is discretely placed, not connected to one another or housed under one transparent pane.

The terminology used in the descriptions of the embodiments herein is for the purpose of describing particular embodiments only and is not intended to limit the claims. The singular articles "a," "an" and "the" are intended to include the plural forms as well, unless the context clearly indicates otherwise. It will also be understood that the term "and/or" refers to and encompasses any and all possible combinations of one or more of the associated listed terms. Similarly, the conjunction "or" is not necessarily mutually exclusive.

References will now be made in detail to embodiments, accompanied by numerals that correspond to appropriate parts of the figures. Examples will be provided to illustrate the various ways the present invention may be utilized. Specific details will be set forth to provide a thorough understanding of the present invention. However, it will be apparent to those with ordinary skill in the art that the present embodiments may be practiced without these specific details. In other instances, known methods, procedures and components have not been described in detail to avoid unnecessarily obscuring aspects of the embodiments.

[Theory: reflect light off tumor tissue, increase accuracy with secondary factors—water, Hg, PE, PC)] When a beam of light interacts with a material, e.g., a tumor, part of it is transmitted, part it is reflected, and part of it is diffracted (scattered). Various scattering types result based on the size of the particle and the wavelength of the incident radiation, though it occurs at all wavelengths of the electromagnetic spectrum. The equation to determine the scattering type is described by: $\alpha = \pi D_p / \lambda$, where $\pi D_p$ is the diameter of the particle, and A is the wavelength of the incident radiation. The value of $\alpha$ determines the domain of the scattering type. If $\alpha \ll 1$, it is Rayleigh scattering, in which the particle is very small compared to the wavelength. If $\alpha \approx 1$, it is Mie scattering, in which the particle is about the same size as the wavelength. If $\alpha \gg 1$, it is geometric scattering, in which the particle is much larger compared to the wavelength. Particles with sizes very small ($r<\lambda/10$) compared to the wavelength of incident radiation, scatter uniformly into both the forward and backward direction. Over 99% of the scattered radiation has the same frequency as the incident beam. Thus, incident light that has diffracted is identifiable by its wavelength. Mie and Rayleigh scattering types exhibit this type of behavior. A small portion of the scattered radiation has frequencies different from that of the incident beam: Raman and Brillouin scattering have forms of inelastic scattering. Fluorescence of light occurs where a substance that has absorbed light or other electromagnetic radiation and emits light, which is lower energy than the absorbed radiation, unless the absorbed electromagnetic radiation is sufficiently intense. The two-photon absorption process helps fluorescing light emit radiation having higher energy after absorption. In the present invention, single-photon absorptions and/or two-photon absorptions can be used to further verify the type and dimensions of the cancer tissue. According to this invention, two-photon absorptions help detect the cancer cells that exist deeper in the body and identify the size and type of tissues.

Reflection or refraction of light may occur whenever light travels from a medium of a given refractive index into a medium with a different refractive index. Total internal reflection occurs when light strikes a medium boundary at an angle larger than a particular critical angle with respect to the normal to the surface. If the refractive index is lower on the other side of the boundary, no light can pass through and all of the light is reflected. The critical angle is the angle of incidence above which the total internal reflection occurs. Diffuse reflectance may occur at boundaries of different substances or particles, where light is partially reflected (few percent intensity) while passing the boundary. Refraction of light is described by Snell's law: The angle of incidence $\theta_1$ is related to the angle of refraction $\theta_2$ in another medium by $\sin\theta_1/\sin\theta_2 = n_2/n_1$, where n is the refractive index.

Photon propagation in tissue can be further described by five variables: 3 spatial coordinates to describe the position (Cartesian coordinates) and 2 directional angles to describe the direction of travel (spherical coordinates). The relationship between penetration depth of light and its wavelength can be described by: Effective penetration depth=$1/\mu(\text{eff})$; $\mu(\text{eff})$=effective attenuation coefficient=$[3\mu(a) \times (\mu(a) + \mu(s'))]^{0.5}$; where $\mu(s')$=attenuation coefficient=$\mu(s)(1-g)$; $\mu(a)$=absorption coefficient; $\mu(s)$=scattering coefficient; and g=anisotropic properties. The latter optical properties are measurable or known values for a type of tissue material.

Figure 1B:
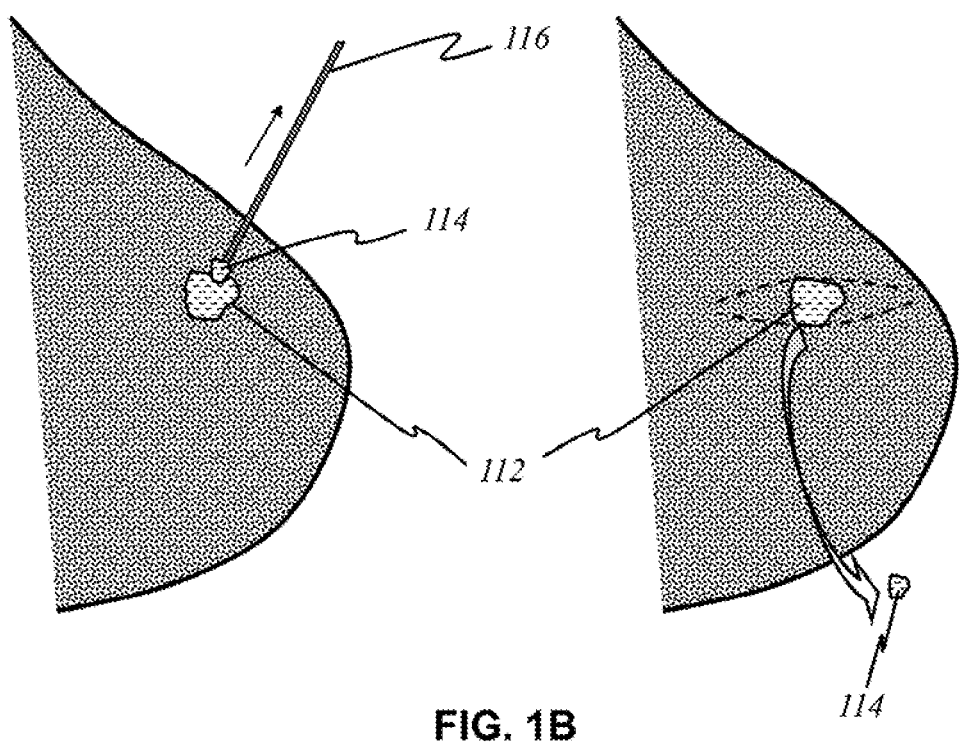
FIG. 1B shows a basic overview of the prior art of biopsy on a breast tissue.

FIG. 1A illustrates a basic overview of the prior art of mammography. It is a technique that involves compressing a breast 102 and utilizing X-rays to create images for review. Breast 102 is placed between a compression paddle 104 and a film table 106. Compression paddle 104 moves to squeeze breast tissue 102, resulting in discomfort and pain to the patient. Compressed breast 108 is then imaged by an X-ray tube 110. The images are reviewed by a physician to locate any suspicious areas for further examination through biopsy. FIG. 1B illustrates basic methods of biopsy procedures on an area of concern 112. The procedure may involve removing a tissue 114 by using a needle 116 or excising it in a more surgical manner. Both methods involve an invasive procedure that removes part of the breast tissue for histological analysis, which, together with the previous procedure, can place physical and emotional stress on the patient.

FIG. 2 is a block diagram illustrating the overarching concept of the present invention. At time to, a light source 200 emits light 202 of a particular wavelength ("uniband") or varying wavelengths ("broadband") into a breast tissue 204. In some embodiments, each source 200 is lined up in a two-dimensional fashion to create an array of sources (see below). Each source 200 may emit a certain wavelength. In some other embodiments, sources emitting the same wavelength may be grouped into larger panels. In yet other embodiments, each source 200 may emit a range of wavelengths. A source driver 206 drives source 200 and selects the pulse duration to be operated. Source 200 can be operated in continuous wave (CW) or pulse operation based on the necessities, and it converts electric signals to optical signals. A controller 208 receives instructions to provide signals to a source driver 136, which operates a specific source. Alternatively, controller 208 also receives instructions to operate the sources having specific wavelengths and/or specific ranges of wavelengths in either pulse or CW operation. According to this invention, alternatively, controller 208 can be operated and are instructed by one or more circuit blocks (not shown here) to operate desired source, desired wavelength(s), desired pulse-width/CW, desired intensity, or a combination thereof.

Light 210 returns as a reflection, or scatters and comes back as diffracted, refracted, or scattered light. At time $t_1$, a detector 212 receives returned light 210 of a certain wavelength. Detector 212 converts light 210 into electrical signals, which are sent to a signal amplifier 214. A digitizer 216 turns the amplified signal into digital form. A processing element ("processor") 218 performs calculations that can create three-dimensional images from two-dimensional images. Processor 218 produces other important data. For instance, it determines the location of areas of concern by deriving times of flight $t_1-t_0$ and the size of areas of concern by comparing images from light of different wavelengths. Although some absorption of emitted light 202 occurs, if an object has a size smaller than the wavelength of light hitting it, diffraction and scattering of the light occurs. On the other hand, if an object has a size larger than the wavelength of light, the object reflects the light. Thus, processor 218 may determine the size of potential tumors by collecting images based on light 202 of varying wavelengths. Processor 218 then sends relevant information to a display screen 220 for a user to read.

According to this preferred embodiment, processor 218 operates the transmission elements and the receiving elements (not shown here specifically), and processes the receiving signals based on a build-up algorithm, described later. The transmission elements (not shown here specifically) comprise controller 208, driver 206, and source 200.

Processor 218 instructs the transmission elements and receiving elements, based on its determination of how to operate the source and which part of receiving elements should be processed.

By way of example and without any limitation, in FIG. 2, the source can be operated in various ways using components having the functionality to select the source, wavelength, pulse/CW, and source intensity, and in various ways processor 218 can operate the transmitter elements and receiving elements, as instructed by software, either embedded into processing unit 218, and/or separately operated by a computing unit with or without display element 220 externally interfaced with processor 218.

According to this invention, alternatively, the components as shown in FIG. 2 may be grouped in different locations. The dotted lines above the block diagram indicate how the components may be grouped together. In some embodiments (Embodiment A), light sources 200 and detectors 212 are placed together in a handheld device separate from the module containing processor 218 along with the other components illustrated. The handheld device is henceforth referred to as the "user end"; the latter module is henceforth referred to as the "processor end". During operation, the user directly manipulates the handheld "user end" device over her breast, emitting light 202 and detecting returning light 210. Light 210 that returns to the user end is sent to the processor end (containing processor 218) through electrical, optical, or wireless channels (see FIGS. 21-27). The transmitted signals are then amplified, processed, and may be displayed on screen 220.

According to this invention, in some other embodiments (Embodiment B), light sources 200, detectors 212, and processor 218 are in the processor end. Initial emission and later collection of light are both performed at the processor end. Light 202 emitted from sources 200 and light 210 returned to the detectors 212 propagate through an optical-fiber cable. At the other end of the optical cable is a handheld device on the user end, which the user places, moves, or otherwise manipulates over breast tissue 204. This device delivers light 202 emitted and carried via optical means from sources 200, and then collects and focuses returned light 210 for transmission back through the optical cable to detectors 212. Electrical or wireless means are not used in these embodiments because only optical signals travel between the user end and the processor end.

In yet other embodiments (Embodiment C), light sources 200, detectors 212, and processor 218 are in one device: the user end. All light generation, data gathering, processing, and imaging are done within the handheld device. End result of operation, such as images and other data, are transferred via electrical, optical, or wireless means to display screen 220 or another device, such as a mobile device or a monitor of a computer. Other means of implementation and descriptions of accompanying figures are disclosed below to reveal a closer look at the arrangements of sources 200 and detectors 212.

A diffraction pattern, i.e., an interference pattern that propagates uniformly when a wave or a series of waves undergoes diffraction, results if an obstacle has a size smaller than the wavelength of optical wave encountering the object. The pattern provides information about the frequency of the wave and the structure of the material causing the diffraction. An interferometer can be used to detect the nature of the diffraction pattern.

Functions of above-described embodiments of the handheld device are driven by software programs. There are several main functions. One function of the device can perform a rough spatial scan of the breast tissue to locate possible areas of concern. The rough spatial scan is performed with variation of intensity (thus varying the depth) per unit area per unit time. The scan spatially covers the breast tissue by emitting broadband light, coherent, or incoherent sources, and then collecting any returning light. If light returns, the reflected light has varying patterns—direct reflection, diffraction, fluorescence—based on the size (early stage or later stage), characteristic of the cells (mere calcification, hard-shelled tumor or soft-shelled tumor) the emitted light struck, and the nature of the emitted light. The scan also covers the tissue depth-wise by varying the intensity and/or wavelength of the emitted light. The scan detects tumor-like substances by matching the returning light with known diffraction patterns or spectral profiles of cancerous lesions. It can then continue with a detailed scan and iterations with varying optical parameters in the areas of concern for further analysis and obtaining results, which may include a high-resolution scan, determination of depth and location, construction of a three-dimensional image, and identification of the type of the tissue substance (normal, healthy tissue vs. harmless calcification vs. early-stage tumor). Optical parameters include wavelength, energy fluence rate (flux over time), pulse rate, absorption coefficient, scattering coefficient, refractive index, scattering phase function. Light propagation in scattering and absorbing media can be defined with respect to radiative transfer.

According to one-dimensional transport theory, light propagation in scattering and absorbing media can be defined by integro-differential equation of radiative transfer, assuming 1) optical properties can be measured, 2) light propagation is restricted to +x or −x directions, and 3) the tissue light interacts with is homogenous and isotropic. Optical properties under this model include: $\mu_{a1}$=absorption coefficient for 1D geometry, [m$^{-1}$]; $\mu_{s1}$=scattering coefficient for 1D geometry, [m$^{-1}$]; c=backscattering coefficient where $\mu_{s1}p(+,-)=\mu_{s1}p(-,+)$, [m$^{-1}$]; $p(\hat{x},\hat{x}')$ scattering phase function where $\hat{x}$ and $\hat{x}'$ are directional unit vectors; $F_+(x)$=photon flux in +x direction, [Wm$^{-2}$]; $F_-(x)$=photon flux in −x direction, [Wm$^{-2}$]; E=incident (laser) irradiance, [Wm$^{-2}$]. Accordingly, $\mu_{a1}$ dx=probability that a photon is absorbed when traversing infinitesimal distance dx; $\mu_{s1}$ dx=probability that a photon is scattered into either +x or −x direction when traversing infinitesimal distance dr; $p(\hat{x},\hat{x}')$ $\mu_{s1}$ dx=probability that a photon is scattered from the direction of propagation $\hat{x}'$ into direction z when traversing infinitesimal distance dx. The following equations hold true under this one-dimensional transport theory.

1D transport equations (1) and (2):

$$F_+(x+dx)-F_+(x)=-F_+(x)\mu_{a1}dx-F_+(x)\mu_{s1}dx+F_+(x)p(+,+)\mu_{s1}dx+F_-(x)p(+,-)\mu_{s1}dx \quad (1)$$

$$\frac{dF_+(x)}{dx}=-F_+(x)(\mu_{a1}+\mu_{s1})+F_+(x)\mu_{s1}p(+,+)+F_-(x)\mu_{s1}p(+,-) \quad (2)$$

Backscattering coefficient (3):

$$\sigma=\mu_{s1}p(-,+)=\mu_{s1}p(+,-) \quad (3)$$

Differential photon flux in +x and −x directions, equations (4-1) and (4-2):

$$\frac{dF_+(x)}{dx}=-(\mu_{a1}+\sigma)F_+(x)+\sigma F_-(x) \quad (4-1)$$

$$-\frac{dF_-(x)}{dx}=-(\mu_{a1}+\sigma)F_-(x)+\sigma F_+(x) \quad (4-2)$$

1-D fluence equations (5) and (6), where $m=(\mu_{a1}+\sigma)/\sigma_b$ and $b=\sqrt{m^2-1}$:

$$F_+(x)=E\frac{m\sinh[b\sigma(D-x)]+b\cosh b\sigma(D-x)]}{m\sinh(b\sigma D)+b\cosh(b\sigma D)} \quad (5)$$

$$F_-(x)=E\frac{\sinh[b\sigma(D-x)]}{m\sinh(b\sigma D)+b\cosh(b\sigma D)} \quad (6)$$

Energy fluence rate can be related to depth or distance by equation (7), where L=radiance, [W/m$^2$*sr]; p=phase of scattering function; S=source of power generated at r in direction of $\hat{s}$:

$$\frac{dL(r,\hat{s})}{ds}=-\mu_a L(r,\hat{s})-\mu_s L(r,\hat{s})+\mu_s\int_{4\pi}p(\hat{s},\hat{s}')L(r,\hat{s}')d\omega'+S(r,\hat{s}') \quad (7)$$

Another function of the invention is to determine the wavelengths of the light before it is emitted and whether different wavelengths of light are emitted simultaneously. Individual (uniband) wavelengths may be emitted, scanning the entirety of the target breast tissue one wavelength at a time. With time and effort expended up front, this would narrow down the wavelengths that respond to any potential areas of concern. On the other hand, a range or broadband wavelengths may be emitted. Depending on the range of wavelengths, this method would provide a rough analysis in which a larger scope of potential areas of concern would be collected.

FIG. 3 illustrates an example of an absorption spectrum 300 of light by an arbitrary mass or volume of tissue. As the wavelength of light changes, so does the level of absorption by a material. Shown are two arbitrary wavelengths, $\lambda_1$ and $\lambda_2$. At $\lambda_1$, absorption of electromagnetic wave having wavelength $\lambda_1$ increases. This is an effective wavelength to target with a light source because some absorption is desired to distinguish between emitted light and reflected light, which would have a lower relative intensity than that of emitted light. At $\lambda_2$, absorption of electromagnetic wave having wavelength $\lambda_2$ is high. It may not produce useful images if most of the light is absorbed and not returned to a detector. Based on absorption spectra of particular materials of interest, such as those of breast tumor tissue, water, hemoglobin, lipids abundant in breast tumors (such as phosphatidylethanolamine, "PE" and phosphatidylcholine, "PC"), the light sources are configured in a way that emits a range encompassing relevant wavelengths that would produce useful data. In some wavelengths, either lower than $\lambda_1$ and/or longer than $\lambda_2$, the specific material(s) does not have an absorption and is transparent to those wavelengths.

Light sources may be light-emitting diodes, lasers, or broadband sources. LEDs would have a broader wavelength spectrum, but they are less ideal for generating high-resolution, wavelength-specific data. Lasers offer greater precision and specificity of wavelengths, but their power output should be carefully controlled. Specifically, the full width at half maximum of the spectral width of the LED ($\lambda_1$) would generally be greater than that of a laser source ($\lambda_2$). Broadband sources may be better served by LEDs, while uniband sources may be better served by lasers. Alternatively, according to this invention, broadband sources having broader spectrum than the LEDs, can also be used as source 200. Practical configurations of LEDs, broadband sources, and/or lasers as light sources will be apparent to those having ordinary skill in the art.

Figure 4B:
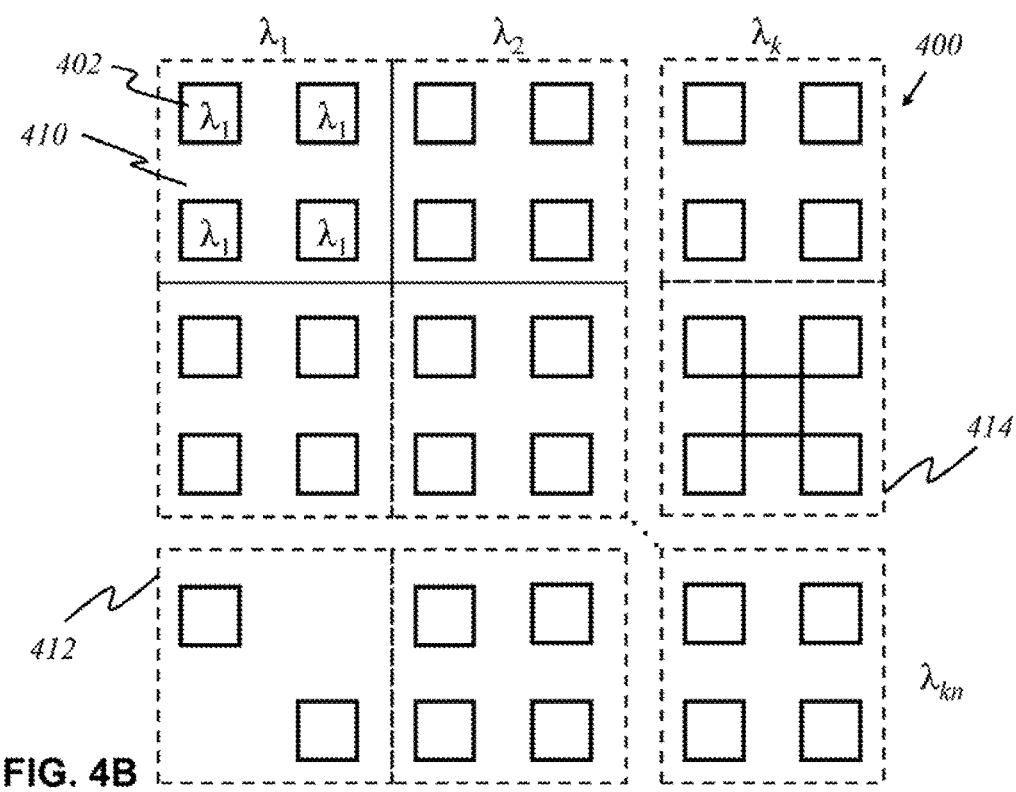

FIGS. 4A-4E and 4G illustrate arrays of light sources (emitters) in various configurations, in accordance to the present invention, wherein like parts are indicated by like reference numerals as used previously, so that repeated explanation is omitted here. FIG. 4A shows an embodiment wherein an array 400 of light sources has k×n array, representing k numbers of light source in x-direction and n numbers of array in y-direction, where k and n are positive integers. In the embodiment illustrated, each source in array 400, produces light of a certain wavelength; every source in array 400 is a unique source that emits light of relevant wavelengths. For instance, the first source 402 produces light of wavelength $\lambda_1$, an adjacent source 404 produces $\lambda_2$, a source 406 adjacent to that produces $\lambda_3$ and so on. No two sources emit the same wavelength in this configuration. The source emitting light of wavelength $\lambda_{kn}$ 408 is the "knth" source that produces a different wavelength. Alternatively, according to this invention, sources having more than one wavelength can be used in the array arrangement (not shown here).

According to this invention, in some other embodiments, shown in FIG. 4B, sources 402 that emit light having a certain wavelength are grouped together in panels 410. Multiple light sources with the same wavelength are employed to increase the resolution of data acquired from reflected or diffracted inbound light. Each panel 410 produces light waves of a unique wavelength, and the panels 410 are arranged in an array of k panels by n panels. Each panel 410 need not necessarily contain the same number of sources 402. There may be panels that contain a fewer or greater number of sources 402, depending on the characteristics and purpose of a particular wavelength. For example, panel 412 has two sources, and panel 414 has five sources.

Figure 4C:
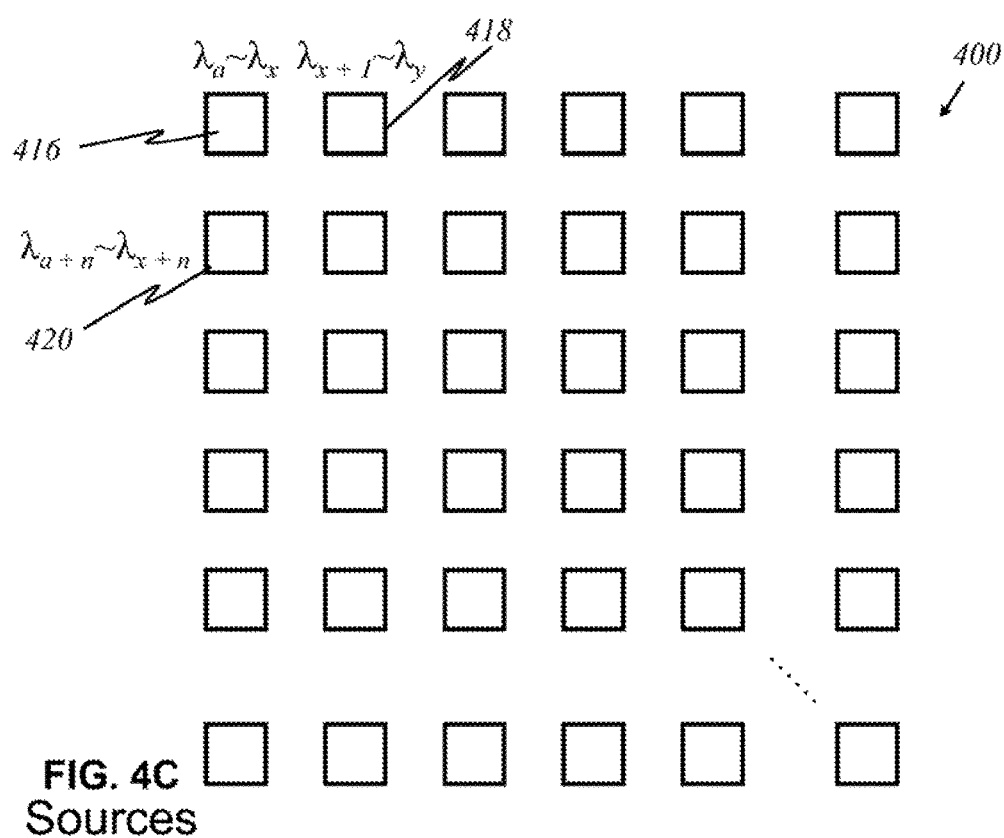

According to this invention, in yet other embodiments, shown in FIG. 4C, alternatively, light sources are broadband sources, which carry multiple signals—that is, emit a range of wavelengths. The ranges of wavelengths of emitted light differ from each other source, and they may overlap. For instance, a source 416 may emit light of wavelengths $\lambda_a$ to $\lambda_x$, where a and x are arbitrary wavelengths. Another source 418 may emit $\lambda_{x+1}$ to $\lambda_y$, where x and y an arbitrary wavelengths, y being greater than x+1. Another source 420 may emit $\lambda_{a+n}$ to $\lambda_{x+n}$, where a+n is between a and x, and x+n is between x+1 and y.

Figure 4D:
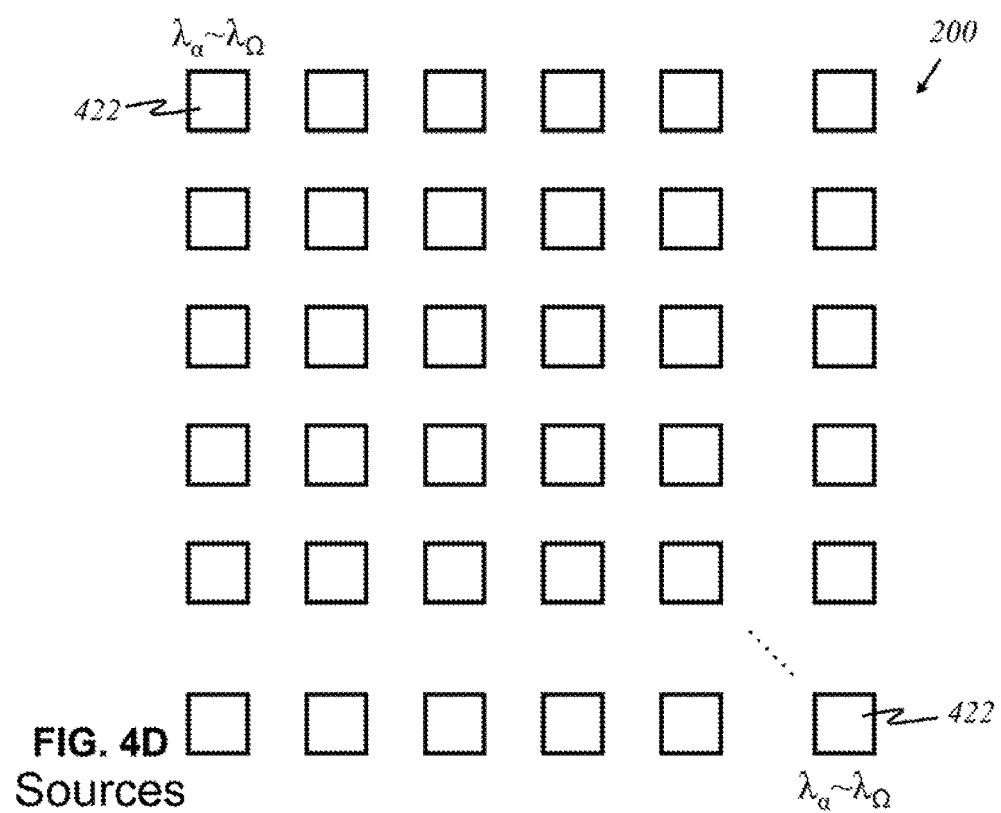
Figure 4E:
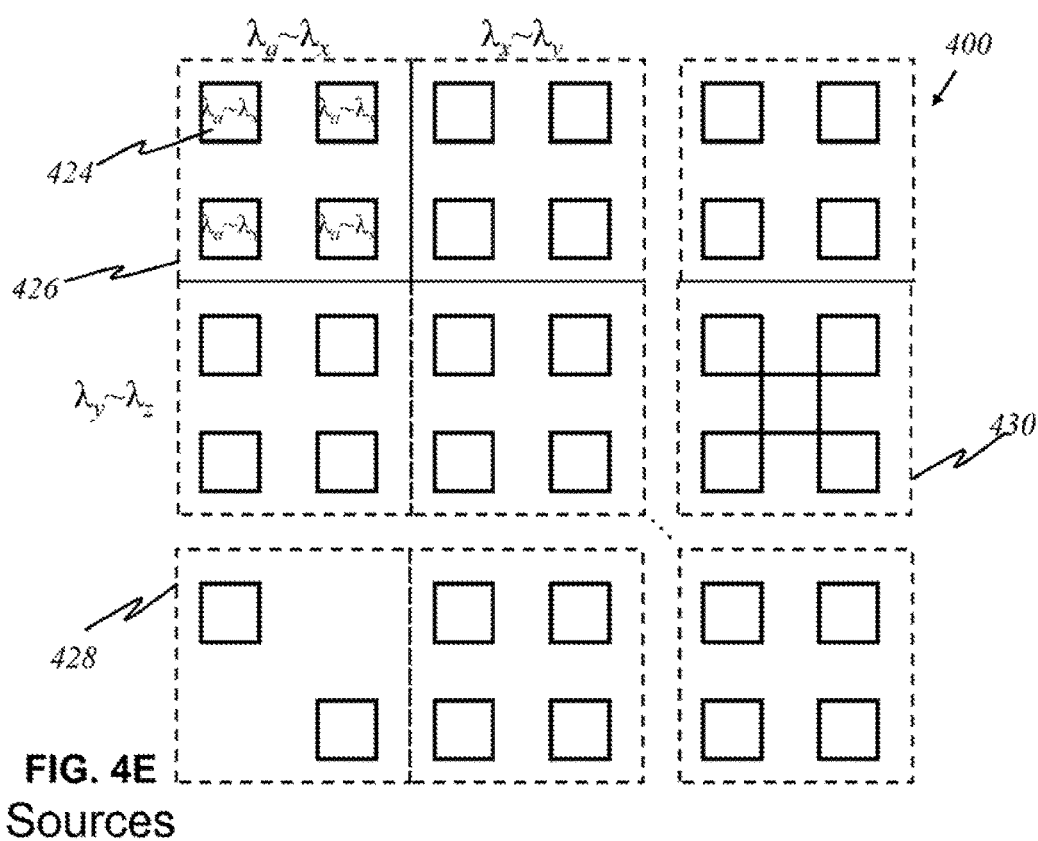

According to this invention, in other embodiments, alternatively shown in FIG. 4D, each source 422 may produce an entire range of desired wavelengths. An array 400 of light sources is shown in FIG. 4D wherein each source 422 produces light of wavelengths $\lambda_\alpha$ to $\lambda_\Omega$, where α is the smallest relevant wavelength desired, and Ω is the highest relevant wavelength desired. Such a source 422 may not emit all wavelengths between $\lambda_\alpha$ and $\lambda_\Omega$, only the relevant ones within that range. Broadband sources 424 may be grouped into panels 426, as shown in FIG. 4E. Similar to the arrangement in FIG. 4B, each panel 426 has sources 424 emitting light of the same range of wavelengths. The number of sources 424 may differ for each panel. There may be panels 428, 430 that contain a fewer or greater number of sources, depending on the characteristics and purpose of a range of particular wavelengths.

Figure 4G:
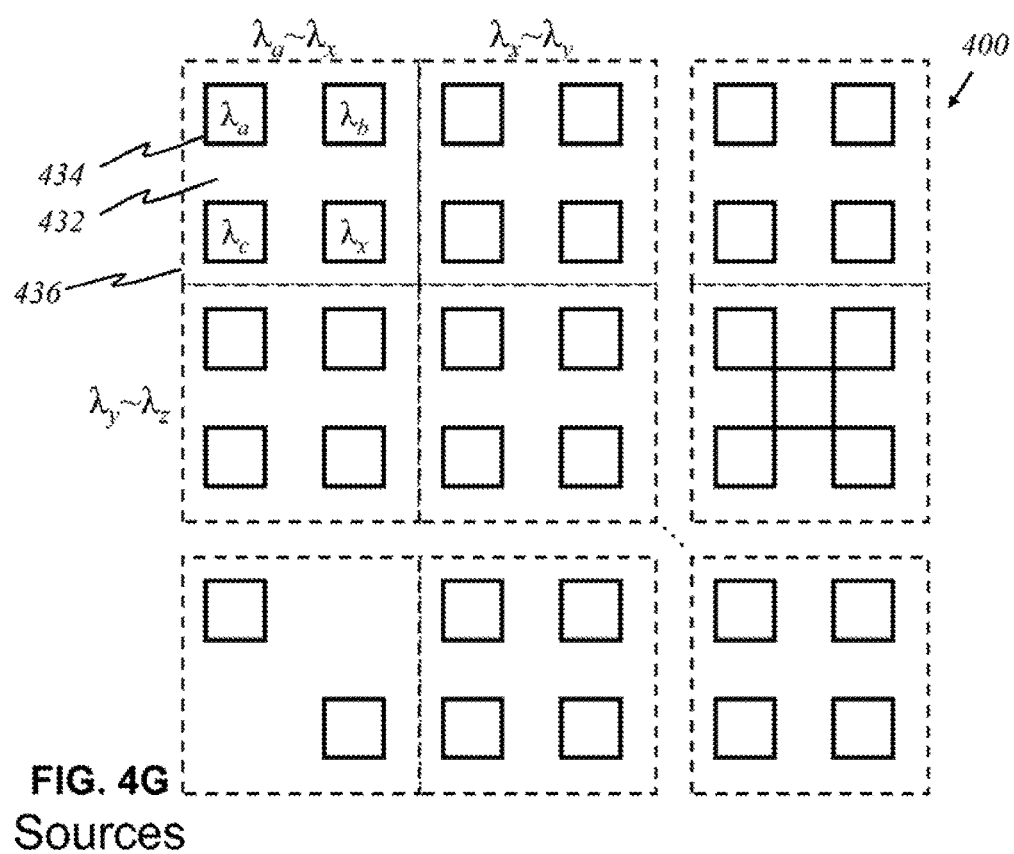

FIG. 4F is an illustration of a light source with a filter 432 that allows certain wavelengths to pass through while blocking other wavelengths in the preferred embodiment, according to this invention, wherein like parts are indicated by like reference numerals as used previously, so that repeated explanation is omitted here. Here, a broadband source 434 generating light 436 of multiple wavelengths $\lambda_1$ through $\lambda_5$ exits through filter 432. Filter 432 has openings that permit light of wavelengths $\lambda_1, \lambda_2, \lambda_3, \lambda_4$, and $\lambda_5$ is to pass through. The result is effectively five light sources that each emits light that is no longer the original light generated by the broadband source. Its utility is illustrated in FIG. 4G, where light sources 434 are grouped together in panels. The number of sources may differ for each panel. There may be panels that contain a fewer or greater number of sources. Each panel comprises an underlying broadband source that produces light waves of multiple wavelengths. For example, underneath upper-left panel 436 is a broadband source that emits light of wavelengths $\lambda_a$ through $\lambda_x$, of which four distinct wavelengths $\lambda_a, \lambda_b, \lambda_c$, and $\lambda_x$ are relevant and of interest. By placing filter 432 over the source panel, one source is simply divided into multiple light sources that effectively function like the individual sources in FIG. 4A.

FIG. 5A illustrates the major components of a light detector 500 that registers light of particular wavelength(s) in a preferred embodiment, according to this invention, wherein like parts are indicated by like reference numerals as used previously, so that repeated explanation is omitted here. Each base detector component 502 is identical in that it detects the presence of light. To detect light of a particular wavelength or wavelengths, a filter 504 installed over the detector varies among each detector 500. Filter 504 blocks out other wavelengths, letting only particular wavelength(s) through. For example, if filter 504 is designed to allow only waves having wavelengths $\lambda_1$ and $\lambda_3$, light having other wavelengths, such as $\lambda_2$, are blocked. Thus, depending on the function of the filter, detector 500 becomes able to detect only desired wavelengths.

FIG. 5B shows a preferred embodiment of an array 506 of such detectors, the array having width k and length n, in accordance to this invention, wherein like parts are indicated by like reference numerals as used previously, so that repeated explanation is omitted here. Each detector 508 can only see and detect the presence of light of a certain wavelength: $\lambda_1, \lambda_2, \lambda_3$, etc. A detector that detects light of wavelength $\lambda_{kn}$ 510 is the "knth" detector that registers that wavelength. If light of a particular wavelength $\lambda_x$ reaches array 506 of detectors, only one detector will recognize it.

Figure 5C:
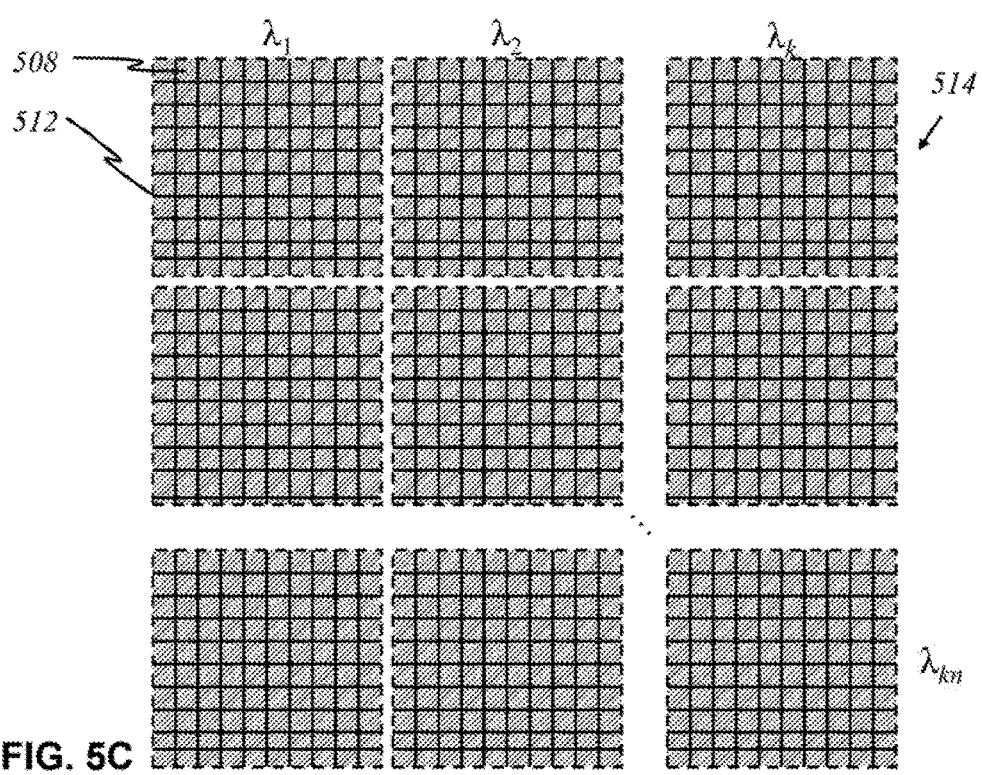

In another preferred embodiment according to this invention, alternatively, detectors 508 that see light of a certain wavelength are grouped together in panels 512, shown in FIG. 5C. Multiple detectors 508 are employed to detect the same wavelength increases the resolution of data acquired by reflected or diffracted light. Each panel 512 detects light of a particular wavelength, and the panels are arranged in an array 514 of k panels by n panels. In some embodiments, however, a filter is unnecessary for a base detector component to detect a particular wavelength; such a detector inherently has the capability to detect a unique wavelength or a narrow range of wavelengths.

Figure 6A:
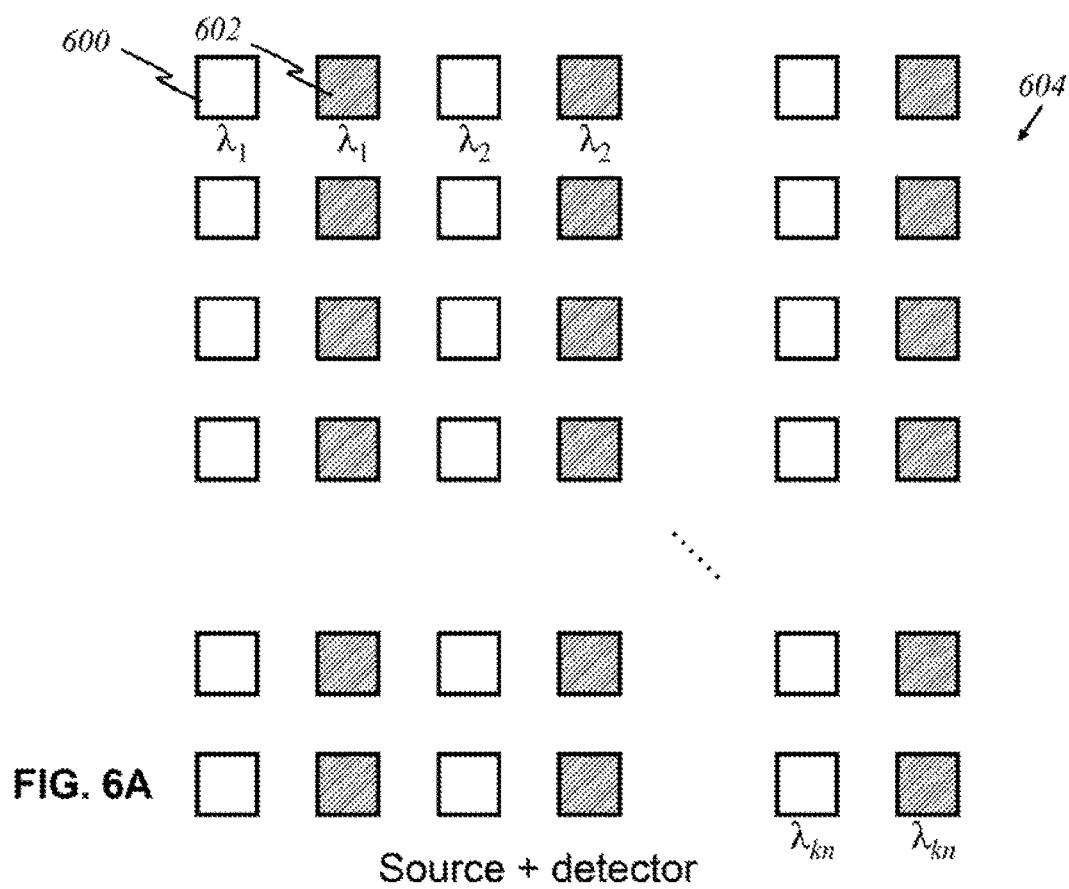

In yet other embodiments, rather than arranging light sources and detectors separately from each other, the sources and detectors can be placed together, as shown in FIGS. 6A-6E. In FIG. 6A, sources 600 that emit light of a certain wavelength and detectors 602 that detect light of a certain wavelength alternate on a source-detector array 604 of width 2k and length 2n.

Figure 6B:
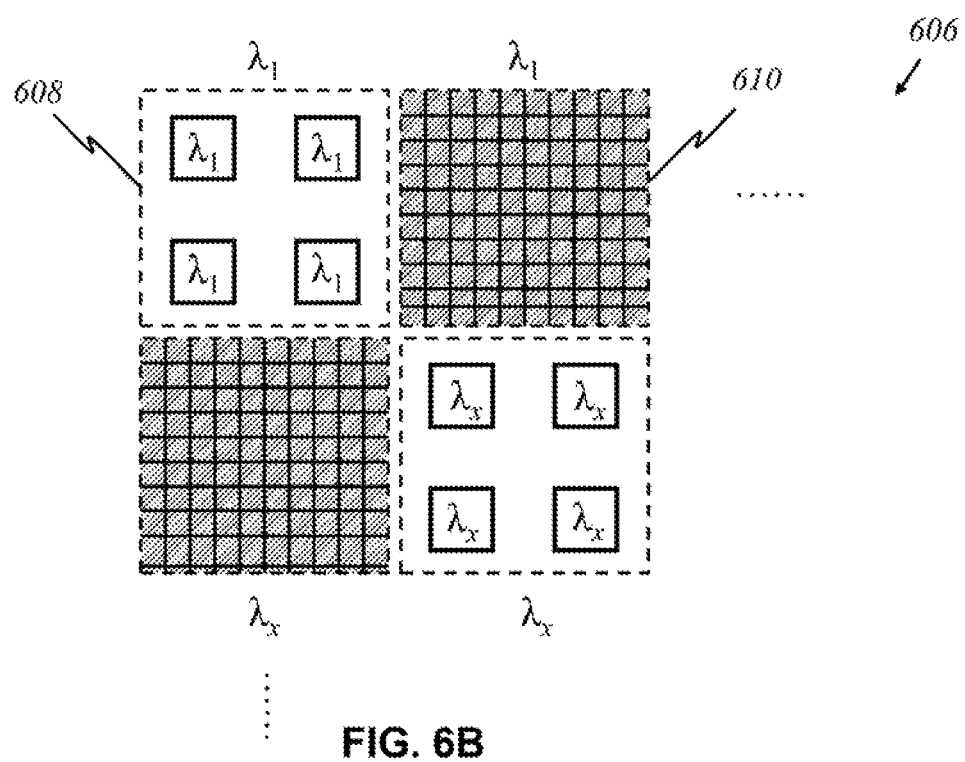

According to this invention, in another preferred embodiment shown in FIG. 6B, panels of multiple sources and detectors, rather than individuals, alternate in a source-detector-panel array 606. A panel comprising sources 608 emitting light of wavelength $\lambda_1$ is adjacent to a panel of detectors 610 that detect only $\lambda_1$. Other panels emitting and detecting light of arbitrary wavelength $\lambda_x$ are arranged similarly.

In another preferred embodiment shown in FIG. 6C, broadband sources and specific detectors are placed in alternating fashion on an array 612 of width 2k and length 2n. Similar to the arrays illustrated in FIGS. 4C-4E, broadband source 614 here may be capable of emitting a narrow range, a wide range, or any range of relevant wavelengths. Each detector 616 or group thereof, however, registers a particular wavelength. One having ordinary skill in the art is able to create further variations in arrangements of light sources and detectors.

Figure 6E:
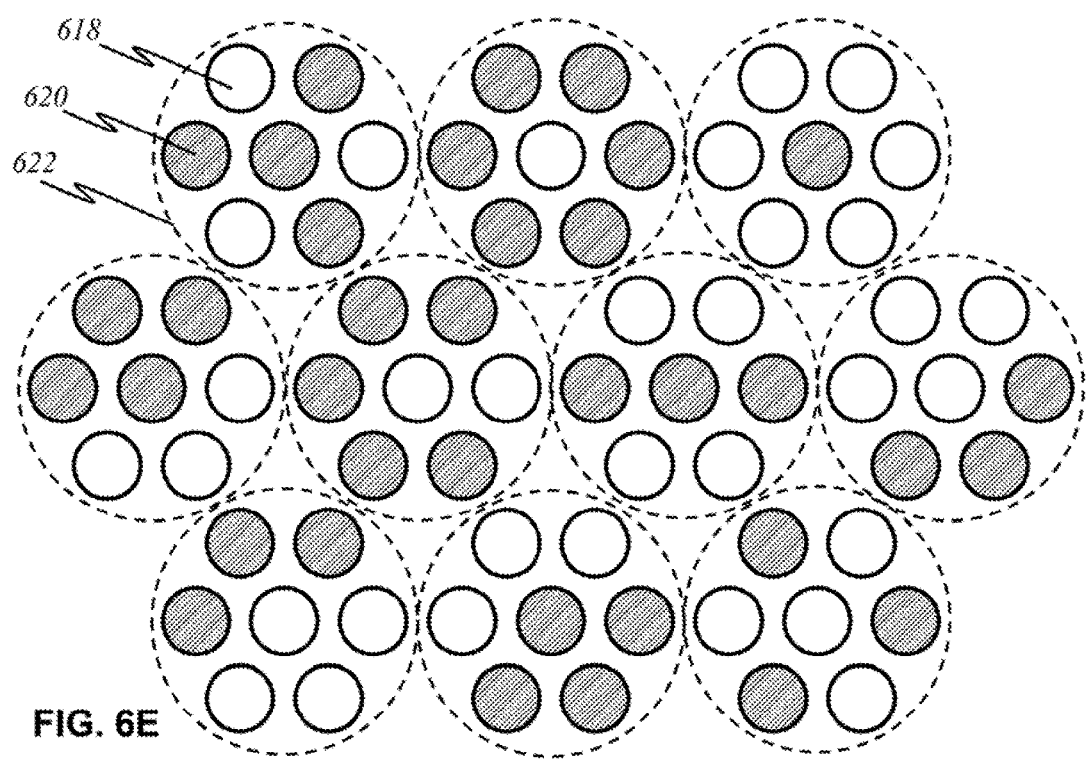

Other arrangements are possible in other embodiments. For instance, FIG. 6D illustrates sources 618 and detectors 620 of circular shape positioned in a space-efficient manner. FIG. 6E illustrates circular sources 618 and circular detectors 620 grouped in various combinations within panels 622. Similar to the previously described embodiments, sources 618 may be capable of emitting a narrow range, a wide range, or a range of relevant wavelengths. Each detector 620 or group thereof detects a particular wavelength. Other possible arrangements, shapes, and configurations (not shown here) will be apparent based on the aforementioned disclosures.

The various arrangements of the elements of the present invention manifested in a device will now be described in further detail. To emit light and detect reflected or diffracted light, light sources and detectors must be arranged in a way to emit appropriate wavelengths of light toward the user's breast tissue and detect light that returns from the user's breast tissue. The device can take numerous forms to provide such functions. In some embodiments, one general shape of the device could be a hemisphere with a hollow interior cavity. In other embodiments, it could be a curved surface for making direct contact with the breast tissue. In yet other embodiments, it could be a more compact device that can flip open and engage panels of sources and detectors. Other arrangements, features, structural dimensions, shapes, materials used, etc., allowing detectors to receive light reflected or diffracted from the breast tissue will be apparent to those having ordinary skill in the art.

Figure 7A:
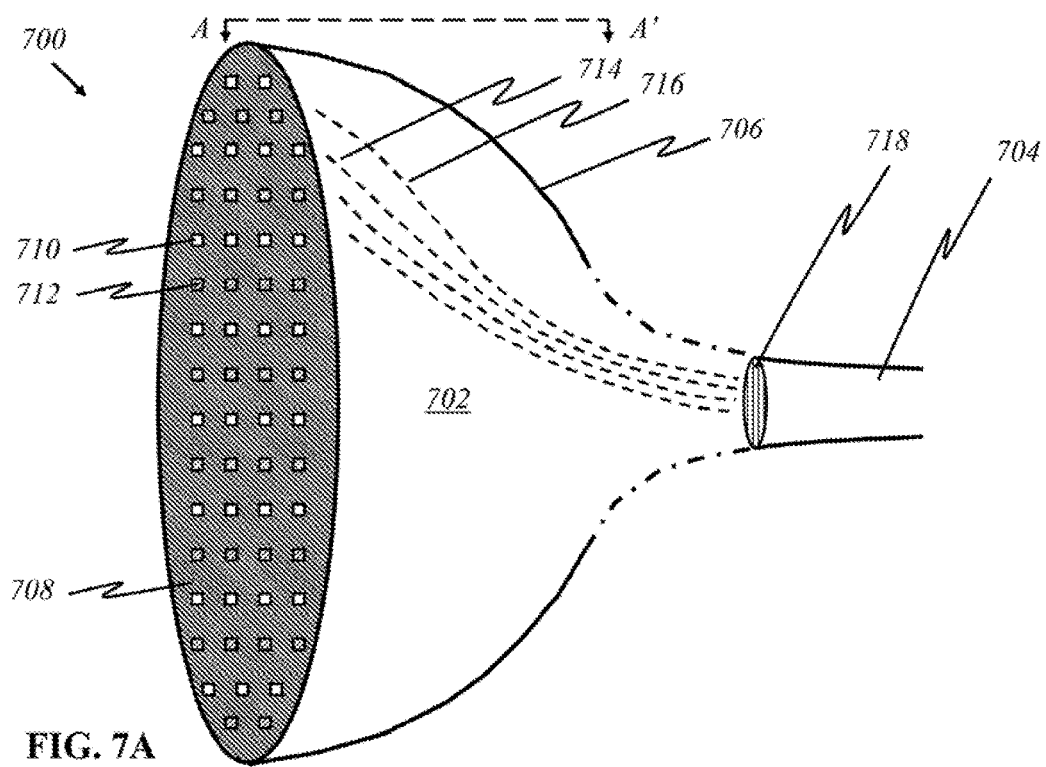
FIGS. 7A and 7B show schematics of a preferred "non-contact" embodiment in an angled view.

FIG. 7A is an illustration showing a schematic diagram of medical device in an angled view in a preferred embodiment ("non-contact embodiment"), in accordance to this invention that does not require complete contact with a patient's breast tissue. A device 700 has a cup 702 in the shape of a hemisphere connected to a mainframe (not shown here) via a cable 704, which represents a bundle of optical fibers, an electronic connection, or a wireless connection. Hemispheric portion 702 is the user end of the apparatus and is handheld. The mainframe contains a processor that enables instructions and generates optical signals (light) or corresponding electrical signals to the handheld device. Outer shell 706 of the device houses all the components required to operate the handheld device itself. Outer shell 706 may be composed of a flexible or semi-rigid (rigid and flexible combination) polymer, or it may be an inflexible solid encasing. The inside of the device is a hollow cavity with enough room for a wide range of breast sizes. The inner cavity has substantial curvature to allow emission of light from many directions. Inner surface 708 of the cavity is lined with numerous light sources and detectors or panels thereof that emit and detect light from panoramic positions, enabling the device to collect enough data at once to image the interior of the breast and any areas of interest. Further details on light paths are given below in discussions of cross-sectional views.

Each source 710 and detector 712 is connected to cable 704. The source-to-cable fibers 714 and detector-to-cable fibers 716 may be optical or electrical in nature. A few optical fibers are illustrated in FIG. 7A in dashed lines. Each optical fiber 714, 716 carries optical signals (light), and each electrical wire carries electrical signals. Light that comes through an optical fiber may be collected and focused by a lens 718, after which the light continues to propagate through cable 704 to be processed by the mainframe. In some embodiments, lens 718 is not needed to focus light; instead, the light to and from the mainframe directly travels between a sensor or detector and the mainframe through optical fibers 714, 716. According to this invention, a focusing element in the form of a micro-lens can be included on the tips of fibers 714, 716, on both sides (not shown here) either as a separate lens array components or as an integrated lens array formed on the tips of the both ends of each fiber 714, 716.

Figure 7B:
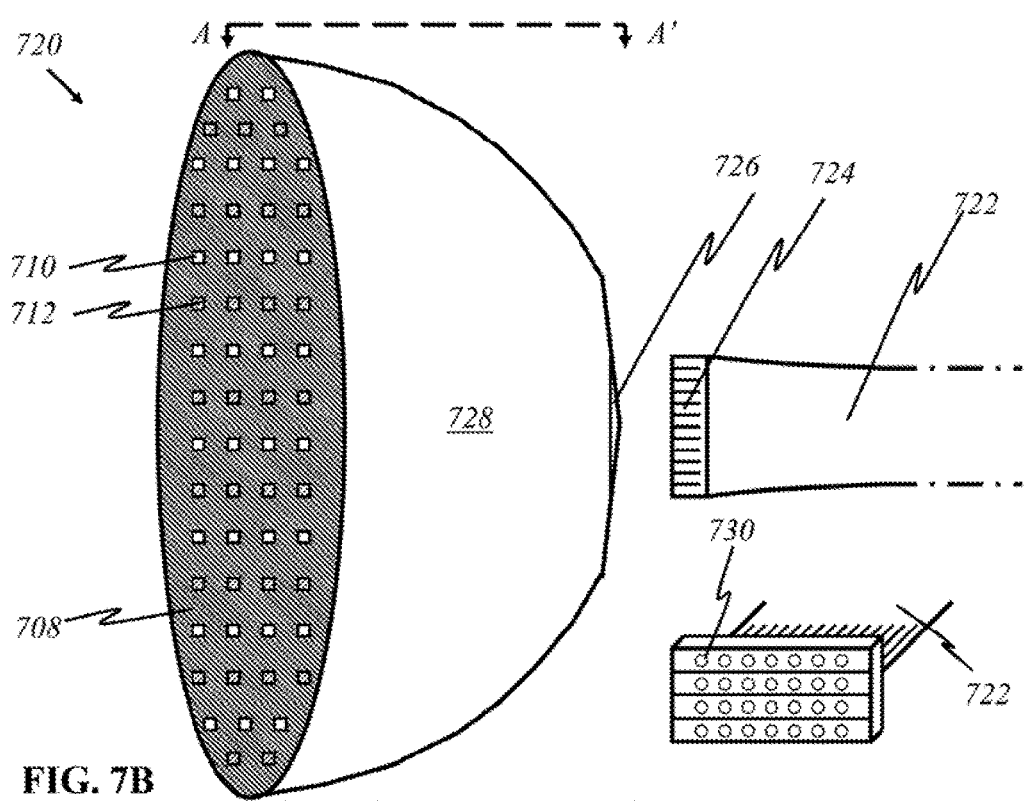

Alternatively, in the non-contact embodiment illustrated in FIG. 7B, data are carried by electrical signals. Like in the embodiment using optical fibers illustrated in FIG. 7A, the inner cavity is hollow and has a surface 708 lined with numerous light sources and detectors or panels thereof that emit and detect light from panoramic positions, enabling the device to collect enough data to image the interior of the breast and any areas of interest. Having electrical wires, detaching a device 720 into separate components enables compact storage. Electric cable 722 is a ribbon cable, whose flat and flexible characteristics encourage mobility and easier storage. In this preferred embodiment, the main difference from the device as shown in FIG. 7A is that there is no lens that focuses light carried by optical fibers. Data are carried by electrical wires that are lined within the outer shell and within device 720.

Electric pins 730 or other means of making contact with circuitry components may also be used as a connection interface alternate to that of the ribbon cable. In some embodiments, device 720 can be connected to the mainframe by inserting a connector 724 of electric ribbon cable 722 into a socket 726 present on outer shell 728 of the device. Socket 726 would have a shape that differs from that for a flat interface, according to the shape of connector 724 shown in FIG. 7B.

FIG. 8A is a schematic showing a cross-sectional view of a preferred embodiment of the user end device taken along A-A' direction of FIGS. 7A and 7B, captured at an arbitrary time in accordance to this invention. In FIG. 8A, wherein a user's breast 800 has been placed into an inner cavity 802 of the device for self-examination. In a simplified representation, four panels 804 of broadband sources (out of at least one broadband source) are symmetrically shown in this embodiment. A panel 806 of detectors (out of at least one detector) is also shown. Source panel 804 and detector panel 806 are not to scale, but it would be possible to contain components as large as those depicted between outer shell 808 and inner cavity 802. For purposes of illustration and not for limitations, only one of the panels of sources emitting light 810, is shown in FIG. 8A. The light emitted is of a broadband spectrum, which carry a range of wavelengths relevant to the analysis of interested materials present (e.g., any tumor tissues, water, hemoglobin, lipids). The outer surfaces of source panel 804 and detector panel 806 are enlarged as shown in FIG. 8B.

Emitted light 810 travels across cavity 802 and interacts with breast tissue 800. Within breast tissue 800, two arbitrary volumes of tissues are illustrated: an area with normal tissue 816 (empty circle) and an area with potentially malignant tissue 818 (hatched circle). Depending on the size of potentially malignant tissue 818, light 810 incident on it, light 810 will be diffracted, reflected, or fluoresced. Assuming that potentially malignant tissue 818 is smaller than the wavelength of emitted light 810, the light will scatter into multiple directions. One such light wave 820 is shown traveling back to inner surface 822 toward panel of detectors 806. If detector 814 is enabled (for example, the filter allows) to detect the particular wavelength of light wave 820, it then processes the signal for imaging or sends it to the mainframe (not shown here) for further processing and imaging. Based on known values of wavelengths that would be returned after reflecting or diffracting from cancer tumors rather than known values of wavelengths that would be returned after reflecting off healthy tissue, the processor can determine the position and depth of the returning light to locate potentially cancerous lesions. Three-dimensional images can also be produced from all returning light waves, with which potential cancerous lesions can be viewed and interpreted on a display.

FIG. 8B is a schematic showing a magnified view of the source panel 804, shown in FIG. 8A. It is an illustrative of 6×6 array of sources 812 embedded, with each source 812 producing multispectral light 810 toward cavity 802. Alternatively, each source 812 in panel 804 can have the fixed wavelength of lights or have different wavelengths, arranged in either 1-D or 2-D array format. Any n by in or n by m array format for sources (not shown here) can be also be used to make source panel 804.

FIG. 8C illustrates a magnified view of detector panel 806. It is an illustrative 6×6 array of detectors 814 embedded, and each detector 814 receiving diffracted, reflected, or fluoresced light 820 from cavity 802, after the light is return from the breast tissue or body surface. Numerous combinations of source 812 and detector 814 placements can be used (not shown here)

FIG. 9 is a schematic showing a cross-sectional view of an alternate preferred embodiment for non-contact embodiment of the user end of the device, taken along A-A' direction of FIGS. 7A and 7B, captured at an arbitrary time according to this invention, wherein like parts are indicated by like reference numerals as used in FIG. 8A, so that repeated explanation is omitted here. The main difference from FIG. 8A is that individual detectors 924 are lined throughout along the inner surface in FIG. 9, rather than grouped in a panel. In a simplified representation, four panels of broadband sources 904 (out of at least one broadband source) are symmetrically shown in this embodiment. A selected number of detectors 930 (out of numerous) is also shown. Multispectral (having different wavelengths) light 910 travels from panel of sources 904 to a user's breast tissue 900 placed in a cavity 902. Within breast tissue 900, two arbitrary volumes of tissues are illustrated: an area with normal tissue 916 (empty circle) and an area with potentially malignant tissue 918 (hatched circle). Assuming that potentially malignant tissue 918 is smaller than the wavelength of emitted light 910, the light will scatter into multiple directions. One such light wave 920 is shown traveling back to inner surface 922 toward detector 924. If detector 924 is enabled to detect the particular wavelength of light wave 920 (for example, the filter allows it), it then processes the signal for imaging or sends it to the mainframe for further processing and imaging.

FIG. 10 is a schematic showing a cross-sectional view of a preferred non-contact embodiment of the user end of the device, taken along A-A' direction of FIGS. 7A and 7B, captured at an arbitrary time, according to this invention, wherein like parts are indicated by like reference numerals as shown in FIGS. 8A and 9, so that repeated explanation is omitted here. The main difference from FIG. 8A is that in FIG. 10, both light sources 1026 and detectors 1024 are placed individually in alternating fashion (1:1, 2:1, or mixed in other ratios) throughout an inner surface 1022, rather than grouped in a panel. In a simplified representation, two broadband sources 1026 (out of numerous) and two detectors 1024 (out of numerous) are shown in this embodiment. Multispectral light 1010 travels from source 1026 to a user's breast tissue 1000. Within breast tissue 1000, two arbitrary volumes of tissues are illustrated: an area with normal tissue 1016 (empty circle) and an area with potentially malignant tissue 1018 (hatched circle). Assuming that potentially malignant tissue 1018 is smaller than the wavelength of emitted light 1010, the light will scatter into multiple directions. One such light wave 1020 is shown traveling back to inner surface 1022 toward detector 1024. If detector 1024 is able to detect the particular wavelength of light wave 1020, it then processes the signal for imaging or sends it to the mainframe for further processing and imaging. From the aforementioned disclosures, other useful configurations will be apparent to those having ordinary skill in the art.

FIG. 11A shows a top view of alternate preferred non-contact embodiment of the device, which has panes that can fold and unfold into compact or useable forms ("flip-open non-contact embodiment"). According to this invention, to make the device compact, the device comprises at least one foldable pane amenable to handheld use and transportation. Alternatively, the device can have more than one pane, wherein each pane 1100, 1102 holds detectors 1104, light sources 1106, or both (see FIG. 11B). In this embodiment, center pane 1100 holds light sources facing breast tissue 1108. Hinges 1110 allow panes 1102 on the side to flip open horizontally along arcs 1112 and be held at desired angles relative to center pane 1100. This results in side panes 1102 facing breast tissue 1108. There may be a handle 1114 or other means to grasp the device during operation.

FIG. 11B is a schematic showing a front view of preferred embodiment for flip-open non-contact device according to this invention, wherein like parts are indicated by like reference numerals as shown in FIG. 11A, so that repeated explanation is omitted here. In FIG. 11B, side panes 1102, having panels of detectors 1104, have been unfolded and are facing outward. Sources 1106 are individually placed on center pane 1100, although they may be grouped together in panels and may be broadband or uniband sources (see FIGS. 4-6). Alternatively other variations of placement of sources 1106 and detectors 1104 are possible, for example, as illustrated in FIG. 11C. Here, the main difference from FIG. 11B is that sources 1106 are individually placed on side panes 1102 instead of one center pane 1100. Center pane 1100 comprises panel of detectors 1104.

During operation of the flip-open non-contact embodiment, the user places the device with panes 1100, 1102 opened over her breast tissue 1108. The user may require manual operation to receive sufficient data to image the interior of breast 1108 and any areas of interest. For instance, the user may slowly move the handheld device vertically or horizontally over her breast over a certain path to "scan" it.

Unlike other preferred embodiments previously disclosed in FIGS. 8, 9 and 10, there is no need to place one's breast inside an unseen cavity of a device. In the embodiment illustrated in FIG. 11A, while the device is in operation, broadband or uniband light sources 1106 from center pane 1100 emit light 1116 of varying wavelengths toward the object placed between the side panes, in this case, breast 1108. In this illustration, one pane 1100 of sources and two panes 1102 of detector panels 1104 make up the handheld device. Reflected or diffracted light 1118 travels back to a detector or panel thereof, on side panel 1102. If the detector is able to detect the particular wavelength of the light wave, it then processes the signal for imaging or sends it to the mainframe (not shown) via optical, electrical, or wireless connection for further processing and imaging. Based on known values of wavelengths that would be returned after reflecting or diffracting from cancer tumors rather than known values of wavelengths that would be returned after reflecting off healthy tissue, the processor can determine the position and depth of the returning light to locate potentially cancerous lesions. Three-dimensional images can also be produced from all returning light waves; thus, potentially cancerous lesions can be viewed and interpreted with human eyes.

One way to protect the user from over exposure to light is to place shields between the user's line of sight and light sources. FIG. 12A is a schematic showing a top view of the preferred embodiment for alternate device, according to this invention, wherein like parts are indicated by like reference numerals so that related explanation is omitted here. The main difference between FIGS. 12A and 11A is that in FIG. 12A, shields 1200 are placed over panes 1100, 1102. Shields 1200 are deployed by unfolding them upward from panes 1100, 1102 along arcs 1202. They may be composed of any material that will not be penetrated by the light wavelengths that are used by the device. Such a material should absorb rather than reflect. Alternatively, shields 1200 can be made from materials that can prevent light from partially or wholly escaping outside, such as a polymer, plastic, nano-composite fiber, carbon fiber, etc. Similar to panes 1100, 1102, shields 1200 can be adjusted and held at desired angles. In the illustration, engaged shields 1200 are locked into a substantially perpendicular angle with respect to panes 1100, 1102. The usage of shields 1200 and placement of breast tissue 1108 within the enclosure created by panes 1100, 1102 and shields 1200 decreases the leakage of light from light sources 1106 (see FIGS. 11B, 11C, 12B, 12C). In turn, the user is less likely to be irritated by light that she may see or by wavelengths that may be harmful to the eyes during operation. The shield can be made from the material the type of which can be selected from the group consisting of polymer, plastic, nano-composite having the capability of absorbing the light having wavelengths to be absorbed. Alternatively, the shield can be made from the material which could be reflective for the light wavelengths of interest. In this case, the secondary reflective light from the shield are made to incident onto the detector(s) array (not shown here) for further processing the signal. The signal can be synchronized or asynchronized with the main detector panel described earlier. In this case, the shields can be designed in such a way that incoming light and outgoing light (reflective) can be same direction or different direction (not shown here). Similar to FIG. 11A, hinges 1110 allow panes 1102 on the side to flip open horizontally along arcs 1112 and be held at desired angles relative to center pane 1100. This results in side panes 1102 facing breast tissue 1108. There may be a handle 1114 or other means to grasp the device during operation.

FIG. 12B is a schematic showing the device with front shield 1200, as shown in FIG. 12A, according to this invention, wherein like parts are indicated by like reference numerals so that related explanation is omitted here. In FIG. 12B, side panes 1102, having panels of detectors 1104, have been unfolded and are facing outward. Sources 1106 are individually placed on center pane 1100, although they may be grouped together in panels and may be broadband or uniband sources as shown in FIGS. 4 to 6. Shields 1200 prevent light emitted by the sources from reaching the user's line of sight which remains obstructed by shields 1200 during normal operation. FIG. 12C is a schematic showing the same embodiment. The main difference from FIG. 12B is that sources 1106 are individually placed on two side panes 1102 instead of one center pane 1100, while center pane 1100 comprises panel of detectors 1104. From the aforementioned disclosures, other useful configurations will be apparent to those having ordinary skill in the art.

FIGS. 13A and 13B are schematics showing the angled views of a preferred embodiment with a self-adjusting cavity, before and after the inner shell conforms to the shape of an object within a cavity 1300 (hereinafter, this embodiment is referred to as a "self-adjusting contact embodiment"), according to this invention. Here, the surface of inner shell 1302 makes direct contact with a breast placed in cavity 1300. In the neutral state, inner shell 1302 is close in proximity to outer shell 1304; inner shell 1302 is nearly at the surface of outer shell 1304. After slabs along inner shell 1302 determine the distance between itself and the breast, as further described below (see below FIG. 14A and accompanying disclosure), inner shell 1302 adjusts its surface to conform to the shape of the breast in cavity 1300. As the inner circumference of inner shell 1302 decreases, an area 1306 between outer shell 1304 and inner shell 1302 stretches, unfolds, or otherwise expands to maintain the physical continuity of the device. The states of the device before and after conforming to the breast are shown in FIG. 13A and FIG. 13B, respectively. The degree to which this adaptability is feasible is at least partly based on the material comprising area 1306 between inner shell 1302 and outer shell 1304. A flexible, rubber-based, or fabric-based material may allow greater movement. A difference in radius is indicated by line 1308. This self-adjustment results in inner surface 1302 directly contacting the breast.

Figure 14A:
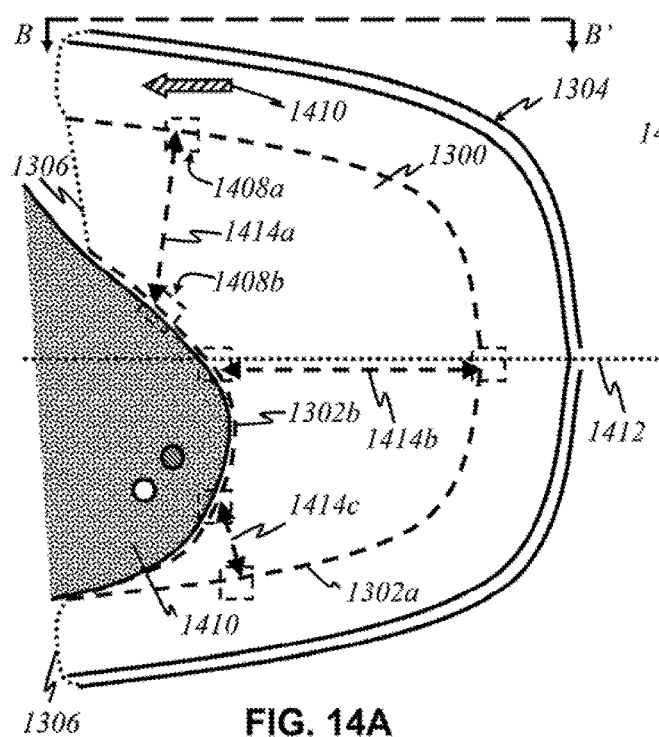
FIG. 14A shows a schematic of the preferred embodiment with a self-adjusting cavity from a cross-sectional view.

FIG. 14A is a schematic showing a cross-sectional view of the self-adjusting contact embodiment of the user end of the device whose inner cavity 1300 self-adjusts to an object (i.e., breast) placed within, taken along B-B' direction of FIG. 13A and FIG. 13B, according to this invention, wherein, like parts are indicated by like reference numerals as used previously, so that repeated explanation is omitted here. Here, inner surface 1302a is comprised of numerous slabs 1400 overlapping one another at least partially. Slabs 1400 are connected in a circular ring that extends circumferentially with respect to a center axis 1412. Each slab 1400 has electrical wires or optical fibers 1402 running along the interior of each slab 1400 and/or between inner shell 1302 and outer shell 1304. Fibers or wires 1402 are connected to sources and detectors (not shown here) on the bottom surface of slabs 1400. The sources and detectors point substantially toward center axis 1412 of cavity 1300 and emit or receive light 1404 along illustrative paths 1406.

Figure 14B:
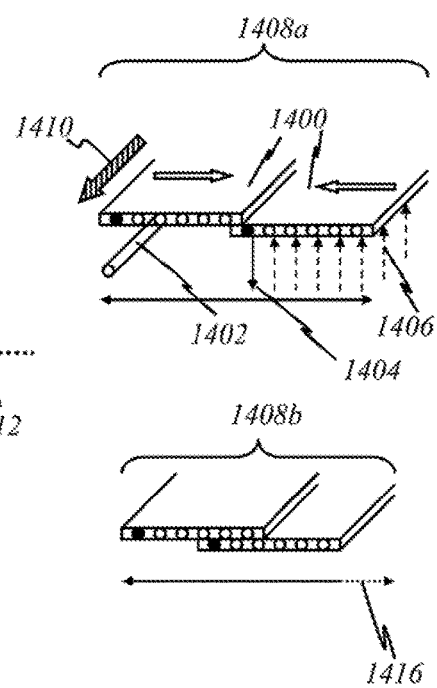
FIG. 14B shows schematics of parts related to the preferred embodiment with a self-adjusting cavity.

FIG. 14B is a schematic showing an enlarged illustrations of slabs 1400 in portions 1408a and 1408b from FIG. 14A, according to this invention. It is a front-top perspective, as if one were looking into the center of cavity 1300, and the two panels are moving sideways relative to that perspective. Slabs 1400 wrap around the circumference of cavity 1300, extending outward and inward relative to the plane of the illustration in FIG. 14B. Guiding arrows 1410 point in the same absolute direction to assist in understanding the orientation of the components. From a front perspective, each ring of slabs 1400 interacts with adjacent rows, which extend inward and outward of the cavity, or farther or closer, respectively, relative to the aforementioned perspective. When slabs 1400 slide under each other the following parameters decrease: distance 1416 between slabs 1400, the circumference and radius of the ring of slabs 1400, and the surface area of inner surface 1302*a*. These changes cause inner shell 1302*a* to move toward center axis 1412 of the device, resulting in a shrunken inner surface 1302*b*.

Each slab has a source that emits light 1404 in the visible range, which allows each panel to determine the distance between itself and the object when the light reflects back. The illustration demonstrates three occurrences of this (in dashed boxes), and the distances calculated between the breast and three slabs are shown. A line 1414*a* indicates the distance between portions 1408*a* and 1408*b*. Other lines 1414*b*, 1414*c* show the distances between other points of inner shell 1302*a* and breast 1410. When the distance between slab 1400 and breast 1410 are recognized, slabs 1400 slide the appropriate distance among themselves, shrinking the surface area of inner shell 1302*a* and thus the volume of cavity 1300. Area 1306 of the device between outer shell 1304 and inner shell 1302 is composed of a flexible material, such as cloth or rubber, or polymer. As the inner circumference decreases, area 1306 stretches, unfolds, or otherwise expands to allow inner surface 1302 to conform to breast 1410. Such self-adjustment results in distances 1414*a*, 1414*b*, 1414*c* approaching zero and shrunken inner surface 1302*b* directly contacting breast 1410.

FIGS. 15A and 15B are schematics showing a front view and an angled view, respectively, of a preferred embodiment of the user end of the device which has a surface 1500 that makes direct contact with the breast ("flexible contact embodiment"), according to this invention. In this embodiment, the device has a broad "C" shape and is connected to a mainframe (not shown here) via a cable 1502, which represents a bundle of optical fibers, an electronic connection, or a wireless connection. The mainframe contains a processor and generates light signals or corresponding electrical signals for the handheld device. The open portion of the device has surface 1500, which is the user end of the handheld apparatus. The interior of the device houses all the components of the handheld device. The outer walls of the device are composed of a flexible polymer or any light and sturdy material. Surface 1500 is curved in a manner that accommodates for almost all breast sizes and curvatures. Surface 1500 is lined with light sources 1504 and detectors 1506 or panels thereof that emit and detect light 1208. The user may adjust the curvature of surface 1500 by bending the top and bottom edges of the device, as indicated by arrows 1512, and the material may allow the device to retain the customized shape for at least a period of time required for self-diagnosis. While surface 1500 possesses substantial curvature, it is also relatively flat compared to the hemispheric embodiments as shown in FIGS. 7A-10. The relatively flat surface causes emission of light waves 1508 in a relatively similar direction with fewer overlapping light waves than would if it were emitted into a cavity as shown in FIGS. 7A-10. Detecting returning light 1510 is also performed by the flat surface. The user may require manual operation of the handheld device to receive sufficient data to image the interior of the breast and any areas of interest. For instance, the user may need to slowly move the handheld device across her breast over a certain path to "scan" it. The distinctions between the embodiments employing optical fibers and electrical wires are disclosed immediately below.

FIG. 16A is a schematic showing a cross-sectional view of a preferred embodiment for a flexible contact embodiment using optical fibers, taken along C-C' direction of FIG. 15, according to this invention. FIG. 16A illustrates a cross-section from FIG. 15 before a breast 1600 makes contact with surface 1500 for optical imaging. The curvature of the interface between breast 1600 and device is more apparent from this perspective. The interior of the device contains individual 1:1 fiber or wire connections 1602 between cable 1502 and a light source or detector.

Each source- or detector-to-cable optical fiber 1602 connects and transfers data from one source or detector on surface 1500 to the mainframe. Between the mainframe and the user end may be a lens 1604 that focuses light signals before sending them through cable 1502. Fibers 1214 are bundled into cable 1502, which connects to the mainframe. The top and bottom edges of the device may be adjusted to user preference by bending it toward and away from the user, as indicated by arrows 1512.

Figure 16B:
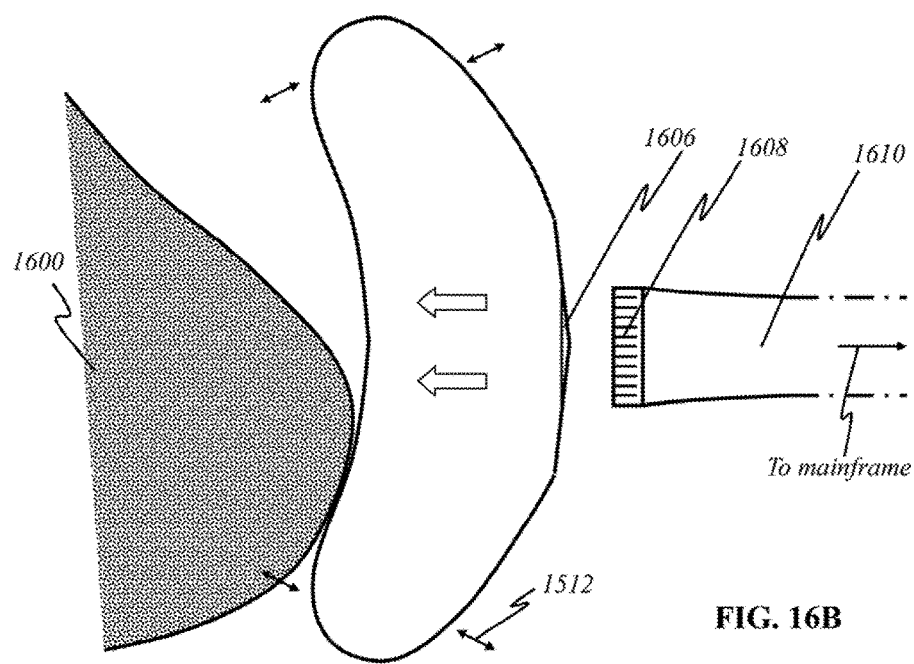

FIG. 16B is a schematic showing the same cross-sectional view of a flexible contact embodiment but using electrical wires. The main difference from FIG. 16A is that in FIG. 16B, a socket 1606 and a connector 1608 for a detachable electric ribbon cable 1610 are used to separate the user end from the mainframe. Electric pins or other means of making contact with circuitry components may also be used (see FIG. 16C). The distinctions between embodiments employing optical fibers and electrical wires are described above for FIGS. 7A and 7B.

Figure 16C:
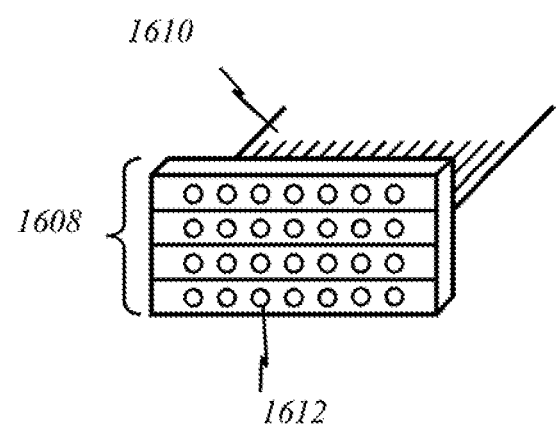
FIG. 16C shows a schematic of a part of a preferred "flexible contact" embodiment.

FIG. 16C is a schematic showing an enlarged view of the front of connector 1608 of electric ribbon cable 1610, which allows connection to socket 1606 via electric pins 1612 as a connection interface alternate to that of the ribbon cable. Socket 1606 would have a shape that differs from that for a flat interface, according to the shape shown in FIG. 16B.

Figure 17A:
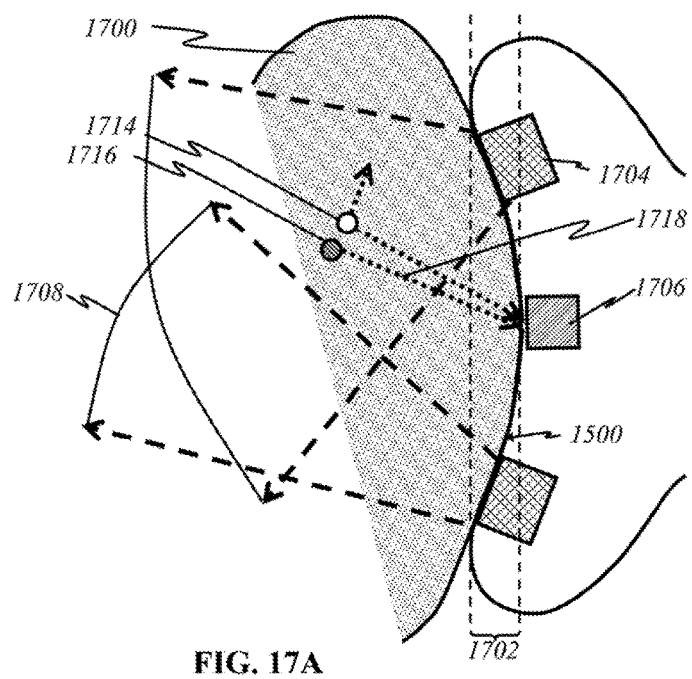
FIG. 17A shows a schematic of a preferred "flexible contact" embodiment in a cross-sectional view after making contact with a breast.

FIG. 17A is a schematic showing a cross-sectional view of a preferred embodiment for a flexible contact embodiment, taken along C-C' direction of FIG. 15 after the breast tissue makes contact with the surface for optical imaging, according to this invention, wherein, like parts are indicated by like reference numerals as used previously, so that repeated explanation is omitted here. Here, the user has pressed the device onto breast 1700 for self-examination. Breast tissue 1700 makes contact with an outside surface 1500 of the device along area 1702. In a simplified representation, two panels 1704 of broadband sources (out of at least one broadband source) are symmetrically shown in this embodiment. They are embedded on outside surface 1500 of the device such that sources 1704 generate and emit optical signals outwardly, and all the components are inside the device, behind surface 1500. Another panel 1706 of detectors (out of at least one detector) is also shown in the same manner. Sources 1704 and detector 1706 are not to scale, but it would be possible to contain components as large as those depicted on the interior side of surface 1500.

For purposes of illustration, each panel of sources 1704 emits light 1708 in different angles. Light 1708 emitted is of a broadband spectrum, i.e., it carries a range of wavelengths relevant to the analysis of interested materials present (e.g., tumor tissues, water, hemoglobin, lipids). The outer surfaces of source panel 1704 and detector panel 1706 are enlarged as shown in FIGS. 17B and 17C as 6×6 arrays of sources 1710 and detectors 1712 embedded in their respective panel surfaces, with each source 1710 producing multispectral light 1708. Emitted light 1708 then interacts with breast tissue 1700. Within breast 1700, two arbitrary volumes of tissues are illustrated: one volume of normal tissue 1714 and one volume of potentially malignant cells 1716 (later determined with greater confidence by analyzing returned information). Depending on the size of potentially malignant tissue 1716, light 1708 hitting it will be diffracted or reflected. Assuming that tissue 1716 is smaller than the wavelength of emitted light 1708, light 1708 will scatter into multiple directions. If tissue 1716 is larger than the wavelength, light 1708 will be reflected. One scattered light wave 1718 is illustrated to be traveling back to interface surface 1500 toward panel of detectors 1706. In reality, light 1718 will be scattered in numerous directions in a spherical shape. If detector 1706 is able to detect at least one particular wavelength, it then processes the optical signal for imaging or sends it to the mainframe for further processing and imaging. Based on known values of wavelengths that would be returned after reflecting or diffracting from cancer tumors rather than known values of wavelengths that would be returned after reflecting off healthy tissue, the processor can determine the position and depth of the returning light to locate potentially cancerous lesions. Three-dimensional images can also be produced from all returning light waves; thus, potentially cancerous lesions can be seen and interpreted with human eyes.

FIG. 18 illustrates a cross-sectional view of another preferred flexible contact embodiment of the user end of the device at an arbitrary time of operation. Like parts are indicated by like reference numerals as used previously, so that repeated explanation is omitted here. The main difference from FIG. 17A is that individual detectors 1800 are lined throughout interface surface 1500, rather than grouped in a panel. In a simplified representation, two panels of broadband sources 1704 (out of at least one broadband source) are symmetrically illustrated in this embodiment. A selected number of detectors 1800 (out of numerous) are also shown. Multispectral light 1708 travels from panels of sources 1704 to breast tissue 1700. Assuming that potentially malignant tissue 1716 is smaller than the wavelength of the emitted light, light 1708 will scatter into multiple directions. One scattered light wave 1718 is illustrated to be traveling back to interface surface 1500 toward one detector 1800. If detector 1800 is able to detect at least one particular wavelength, it then processes the optical signal for imaging or sends it to the mainframe for further processing and imaging.

Figure 19:
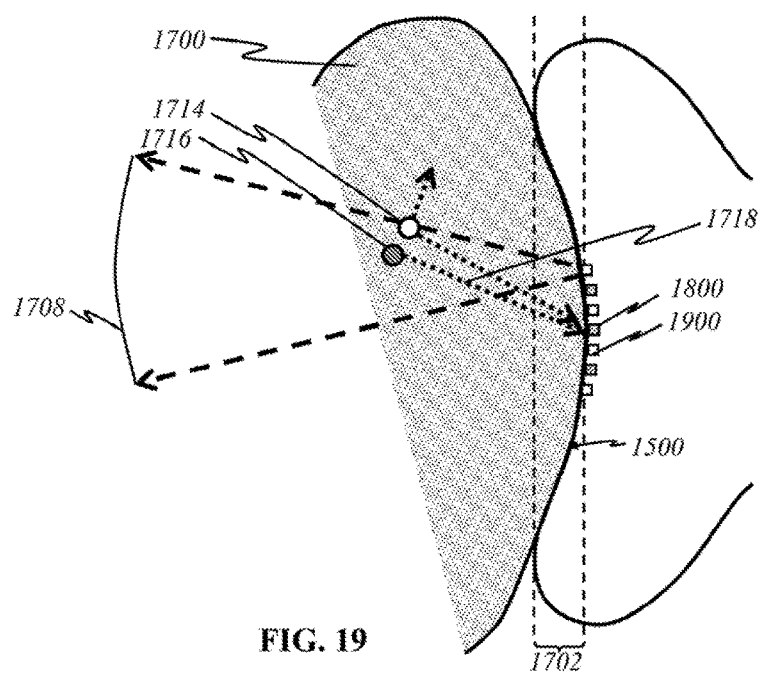
FIG. 19 shows a schematic of another preferred "flexible contact" embodiment in a cross-sectional view after making contact with a breast.

FIG. 19 is a schematic showing a preferred embodiment according to this invention, wherein like parts are indicated by like reference numerals so that repeated explanation is omitted here. The main difference from FIG. 18 is that light sources 1900 and detectors 1800 are placed individually in alternating fashion throughout inner surface 1500, rather than grouped in a panel. From the aforementioned disclosures, other useful configurations will be apparent to those having ordinary skill in the art.

Operational accuracy of the device can be improved by using a supplementary layer between the surface of the breast and the device. Refractive index n plays a role in characterizing biological tissues' response to optical illumination. The layer acts as an intermediary between two media of dissimilar refractive indices. For example, there is a disproportionate disparity between air and tissue if approximately n of air is 1.00, n of epidermis is 1.41, n of dermis is 1.36, and n of fatty tissue is 1.45. A medium with sufficiently disparate refractive index will tend to reflect light incident on that medium. The supplementary layer serves to introduce an intermediate n that mediates and bridges the gap between the disparate values between air and tissue, i.e., approximately between 1.00 and refractive indices of tissue components. Since the light incident must penetrate, the layer is transparent to light wavelengths of interest and reduces reflection. The layer is thin relative to the tissue, non-hazardous to the skin, and is easily removed or washed. The layer helps smooth out the target surface area of the breast, reducing variability and standardizing the experience among users of the device, because there may be different skin types, amount of hair present, and smoothness. Flattening the skin above the area of the breast the device operates on can reduce interference from microscopic obstacles and gaps present on the surface of the skin. The supplementary layer may be embodied and used in various ways as disclosed below.

Figure 20A:
FIGS. 20A-20E show schematics of various forms of a supplementary layer used to improve functionalities of the present invention.
Figure 20B:
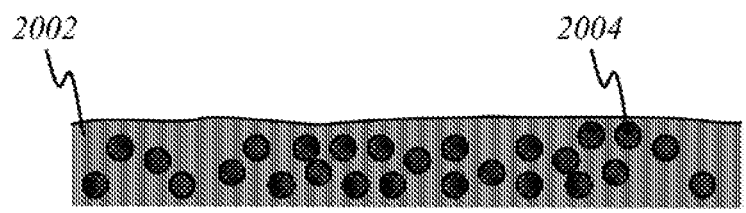

FIG. 20A illustrates a cross-sectional view of a section of skin 2000 above the breast and a gel layer 2002. A thin layer of gel 2002 is applied on the surface of section of skin 2000 over which the device will be placed. The thickness of the layer of gel 2002 is exaggerated to show the amorphous nature of gel 2002. It is easily washed from the skin as well as the device if the device has touched the gel. FIG. 20B is a highly enlarged cross-sectional view of the same section of skin 2000 as FIG. 20A. The main difference from FIG. 20A is that nanoparticles 2004 are embedded in gel 2002, which may be composed of ZnO, TiO2, and/or other metal oxide particles. Nanoparticles 2004 enable reduction or complete alleviation of the reflection of light, which enhances the clarity of images produced later.

Figure 20C:
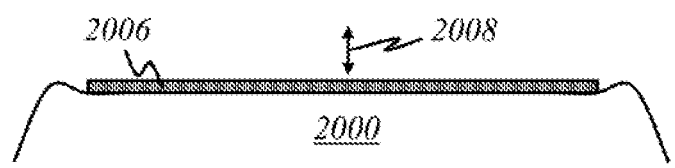

FIG. 20C illustrates a cross-sectional view of skin 2000 and a rigid layer 2006 pressing down on it. As with other forms of the supplementary layer, rigid layer 2006 is transparent to wavelengths of interest and is non-toxic to the skin. By applying force 2008 during application of rigid layer 2006, it flattens skin 2000 and smoothes out the surface of skin 2000. This serves two purposes: Reduce the reflection of light and the delta of refractive indices between air and components of skin 2000, and reduce variability of experience among different users. Rigid layer 2006 may be constructed inexpensively to be disposable.

Figure 20D:
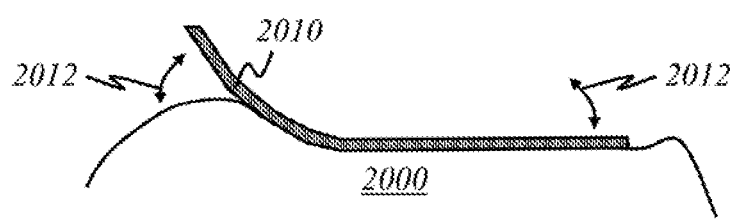
Figure 20E:
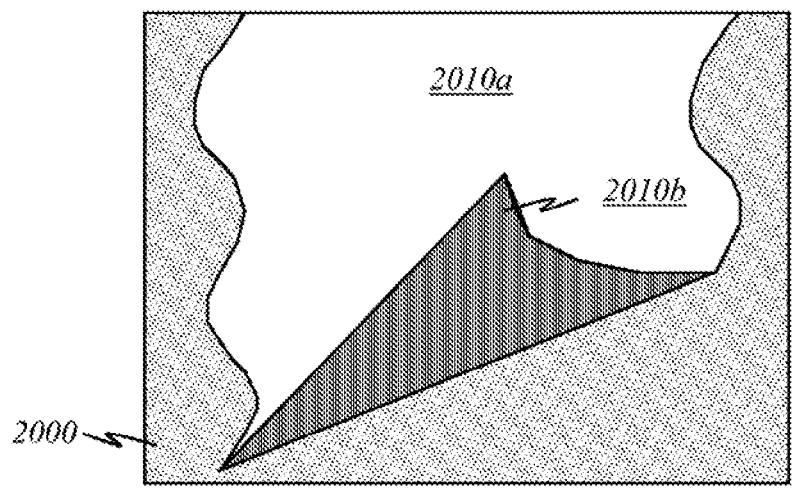

FIG. 20D illustrates a cross-sectional view of skin 2000 and one side of a flexible layer 2010 pressing down on it. As with other forms of the supplementary layer, flexible layer 2010 is transparent to wavelengths of interest and is non-toxic to the skin. Flexible layer 2010 may be extremely thin and malleable so as to be wrapped or stretched over the target area of skin. Similar to the rigid or gel embodiments as shown in FIGS. 20A-20C, flexible layer 2010 is serves to reduce the gap between disparate n values when light enters a different medium. By applying force 2012 toward or away during application of flexible layer 2010, the user has greater control over application of flexible layer 2010 as well as determination of which area of skin to apply it to. Flexible layer 2010 may be constructed inexpensively to be disposable. FIG. 20E is a schematic showing a top view of skin 2000 and a flexible layer 2010 as an alternative view of FIG. 20D. Top side 2010a of flexible layer 2010 is shown, and bottom side 2010b is shown being lifted from skin 2000. Flexible layer 2010 is malleable enough to be folded and partially bent upward as illustrated.

FIG. 21 is a schematic showing a whole view of implementations of operational parts of the preferred embodiment, according to this invention. A user end 2100 is the handheld portion for the user to aim and receive light. In embodiments using optical fibers to transfer light signals, light 2102 may be generated by sources placed in a mainframe 2104 rather than user end 2100). Likewise, detectors may be placed in mainframe 2104 rather than user end 2100. In other embodiments, sources and detectors may be placed on user end 2100, with a generic connection 2106*a* transferring data between the user end and the mainframe. Instructions or data 2108 containing instructions to emit light 2102 may travel from mainframe 2104 to user end 2100. Data 2110 on received light 2112 may travel from user end 2100 to mainframe 2104. Mainframe 2104 may include a processor 2114 and also other components, such as light sources, detectors, display screen, source driver, controller, signal amplifier, and digitizer (see FIG. 2). Different means of transferring data are possible. In some embodiments, connection 2106*a* between mainframe 2104 and user end 2100 is comprised of a bundle of optical fibers that transfer light. In some other embodiments, the connection is comprised of electrical wires, preferably a ribbon cable because it is highly compact and flexible. In yet other embodiments, the connection is wireless and lacks a physical connection.

In some embodiments, a display screen 2118 displays diagnosis results, images, and other information 2116 the user may be interested in. Display screen 2118 may be part of mainframe 1504, exist remotely on another apparatus dedicated to the device, or be on the user's separate electronic device, such as a mobile phone or a personal computer. User end 2100 communicates with mainframe 2104 to exchange data and instructions 2108, 2110. Various embodiments have different combinations wherein components are placed in different places, as described below.

FIG. 22 is a schematic of a whole view of an embodiment, according to this invention, wherein connection 2106*b* between user end 2100 and mainframe 2104 is of electrical nature. Like parts are indicated by like reference numerals as used previously, so that repeated explanation is omitted here. The means of connection transfer only electrical signals. It delivers instructions 2108 from processor 2114 within mainframe 2104, enabling particular sources on user end 2100 to emit light 2102 at predetermined, particular wavelengths and/or predetermined, particular times as instructed. The detectors on user end 2100 register various reflected or diffracted light waves 2112. Data collected 2110 is transferred back to mainframe 2104, where useful data, such as sizes of areas of interest, depths of areas of interest, and images of the interior of the user's breast, are derived. Results derived 2116 can be displayed on screen 2118 for the user. Screen 2118 may be part of mainframe 2104, separate from mainframe 2104, or it could be on another device. For example, the screen may be on a mobile phone or a monitor of a personal computer may connect to mainframe 2104 and serve as the screen. Results 2116 may be sent to such a separate device, or it may be displayed on screen 2118 as part of mainframe 2104.

FIG. 23 is a schematic of a preferred embodiment, according to this invention, wherein like parts are indicated by like reference numerals as used previously, so that repeated explanation is omitted here. The main difference from FIG. 22 is that here, results 2116 are transferred to and displayed on a separate device or screen 2118, whereas all functions described in FIG. 22 are performed at the user end, i.e., user end 2100 contains the processor, sources, and detectors. Display screen 2118 is electrically connected to user end 2100.

FIG. 24 is a schematic diagram of a whole view of an embodiment, wherein the connection between user end 2100 and mainframe 2104 is of optical nature, able to transfer light. Like parts are indicated by like reference numerals as used previously, so that repeated explanation is omitted here. Here, instructions originate from user end 2100, and the sources operate to emit light 2102 at predetermined, particular wavelengths and/or predetermined, particular times. User end 2100 collects returning light waves 2112, which are directly transferred to mainframe 2104 via optical-fiber cable 2106*c*. Light received 2112 at the user end may be focused by a lens (not shown here) before being directly transferred through optical-fiber cable 2106*c*. Received optical signals 2112 are detected by detectors 2120, or a panel thereof, within mainframe 2104. Detected optical signals are processed to derive useful data 2116, such as confirming possible tumors, its size and location, and images of the interior of the user's breast tissue. These data 2116 may be presented on display screen 2118. Screen 2118 may be part of mainframe 2104, separate from it, or it could be on another device. For example, the screen may be on a mobile phone or a monitor of a personal computer.

As a variation of this embodiment, in FIG. 25, optical-fiber cable 2106*c* transfers both emitted light 2102 and returning light 2112. Like parts are indicated by like reference numerals as used previously, so that repeated explanation is omitted here. The main difference from FIG. 24 is that in this embodiment, mainframe 2104 comprises both sources 2122 and detectors 2120. Using the unique properties of optical fibers, optical-fiber cable 2106*c* acts as a waveguide for light 2102, 2112 emitted from and returned to mainframe 2104, where the data is processed. In this embodiment, user end 2100 does not have any sources or detectors. It only acts as a mechanism to collect and focus light that is emitted and returned. As in the embodiment of FIG. 24, results 2116 may be sent to a separate device, or it may be displayed on screen 2118 as part of mainframe 2104.

FIG. 26 is a schematic of a preferred embodiment wherein the connection between user end 2100 and mainframe 2104 is wireless. Instructions 2108*c* to generate light 2102 and data 2110*c* on detected light 2112 are transmitted by wireless means. Instructions 2108*c* are generated from mainframe 2104, enabling particular sources on user end 2100 to emit light 2102 at predetermined, particular wavelengths and/or predetermined, particular times as instructed. The detectors on user end 2100 register various reflected or diffracted light waves 2112. Data 2110*c* collected is transferred wirelessly back to mainframe 2104, where useful data 2116, such as sizes of areas of interest, depths of areas of interest, and images of the interior of the user's breast, are derived. The results derived can be displayed on screen 2118 for the user. Screen 2118 may be part of mainframe 2104, separate from it, or it could be on another device. For example, the screen may be on a mobile phone or a monitor of a personal computer. [additional technical details on wireless functions?].

FIG. 27 is a schematic diagram of an embodiment in which all functions described in the previous FIG. 26 are performed at user end 2100, i.e., user end 2100 contains the processor, sources, and detectors. Like parts are indicated by like reference numerals as used previously, so that repeated explanation is omitted here. The main difference from FIG. 26 is that results 2116 are transferred, not from a separate mainframe but directly from user end 2100, to and displayed on a separate device or screen 2118. Display screen 2118 is connected to user end 2100 via wireless means.

FIG. 28 is a schematic showing a close-up view of an optical-fiber cable 2800, which comprises a bundle of optical fibers 2802. Numerous optical fibers 2802 are packed into cable 2800. Optical fibers 2802 are transparent and highly flexible fibers that are typically at most 0.5 mm. They can function as a waveguide for light 2804 traversing through. Containment of light 2804 is enabled by total internal reflection, which completely reflects light propagating along fiber 2802 hits the boundary of fiber 2802 at a critical angle, ideally close to parallel with the walls of fiber 2802. To confine and propagate light 2804 within fiber 2802, the light that enters cable 2800 must be within a certain range of angles, which a lens (see FIGS. 7A, 16A) assists with.

Figure 29A:
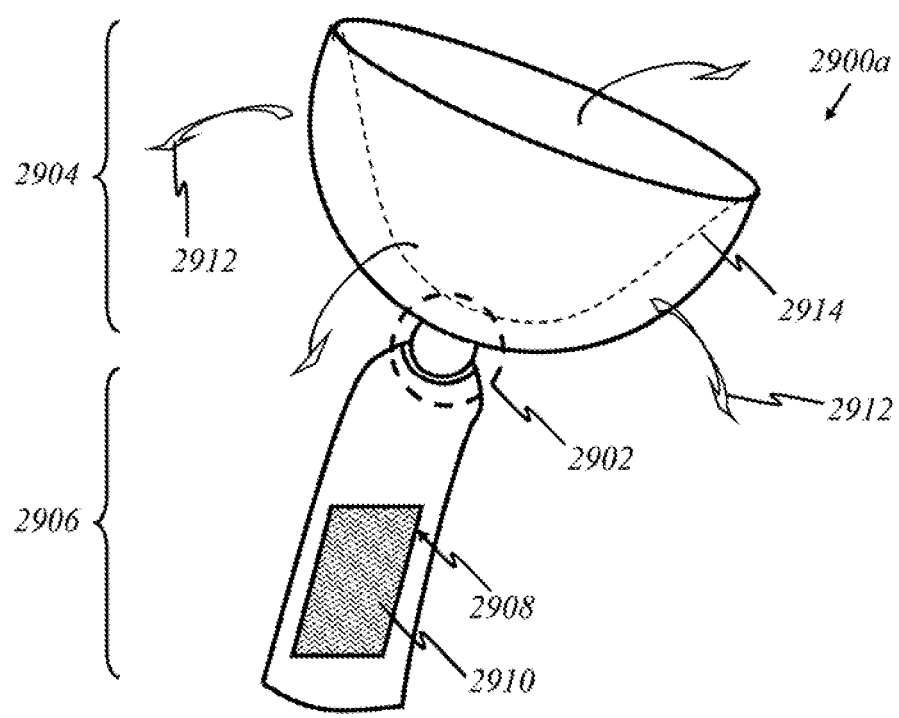

FIGS. 29A-29C are schematic diagrams of various examples of shapes of devices and manufactures in which the functions disclosed thus far may be implemented. FIG. 29A shows an example of an embodiment of a device that implements the present invention. A satellite-shaped device 2900a having a ball-and-socket joint 2902 between a user end 2904 and a handle 2906 is shown. User end 2904 is cup shaped and may implement at least the non-contact and contact embodiments shown in FIGS. 7A-10 and 13-19, enabling versatile use for multiple purposes and usage methods. In this embodiment, a control panel 2908 is shown on handle 2906, but it may be placed anywhere that allows convenient operation. Control panel 2908 may also include a display screen 2910. Control panel 2908 may include user-controlled switches that enable certain functions, such as a power button, an operation button that moves user end in various directions shown by arrows 2912, an operation button that enables an inner surface 2914 to conform to the size of the user's breast, and other peripheral devices. Other configurations and arrangements of elements shown here are possible and will be apparent to those having ordinary skill in the art.

FIG. 29B shows another example of an embodiment of a device that implements the present invention. A top view of a flip-open non-contact type device 2900b having a center pane 2916 and side panes 2918 is shown. As described in the text accompanying FIGS. 11-12, each pane 2916, 2918 has sources or detectors, or both, or panels thereof. The capability to adjust pane angles introduces compactness and flexibility in operating the device depending on the size and location of the breast. This type of device may implement at least the flip-open non-contact embodiments shown in FIGS. 11-12.

FIG. 29C shows another example of an embodiment of a device that implements the present invention and may implement at least the contact embodiments shown in FIGS. 15-19. A side view of a flexible contact device 2900c having a user end 2920 is shown. An interfacing side 2922 of flexible user end 2920 has a curved shape. Flexible user end 2920 allows the user to press device 2900c conform the breast to the shape of interfacing side 2922 of user end 2920. To an extent, user end 2920 may conform to the shape of the breast by virtue of its flexible construction. Direct contact enhances the quality of data acquired with a smaller margin of error. An example of a port 2924 is shown for connecting user end 2920 to other devices, such as a switch, control panel, display screen, computing device, and other peripheral devices, all of which may reside within user end 2920.

Features present in FIGS. 29A and 29C may be modified or combined in other ways. For example, the satellite-shaped device of FIG. 29A may not have a rotatable ball-and-socket joint 2902, fixing the open cavity to one direction. For example, the flexible user end of FIG. 29C may be attached to an elongated handle similar to handle 2906 in FIG. 29A.

The present invention is expected to be found practically use in the hand held based non-invasive cancer screening system where the broadband radiation is used to diagnosis initial stage of the cancer diagnosis, covering breast, skin, etc. The application includes not only hand held type diagnosis system, but also combining with other detection system to increase the accuracy for the small to medium scale system.

Specific embodiments or examples, given in the detailed description of the present invention, are only used for clarifying the technical contents of the present invention, and are not narrowly interpreted in a limited manner to such specific examples, and various modifications may be made therein within the spirit of the present invention and the scope of the following claims.

What is claimed:

1. An imaging system for screening and diagnosis of breast cancer comprising:
    an assembly comprising a receptacle configured to contain and directly contact a biomass;
    a light source configured to emit one or more optical signals each comprising a plurality of wavelengths, the light source comprising a first light detector;
    a second light detector, the first and the second light detectors each being configured to detect returning optical signals, and each configured to convert the returning optical signals to electrical signals; and
    a processing apparatus configured to:
        cause the light source to emit a first optical signal, the first optical signal having a first wavelength, the emission of the first optical signal causing an emission of a first returning optical signal from interaction with a target volume of tissue, the target volume of tissue being a portion of the biomass;
        determine whether the first returning optical signal has diffracted or reflected from the target volume of tissue based on the first returning optical signal from the target volume of tissue being detected by either or both of the first light detector and the second light detector;
        responsive to a determination that the first returning optical signal has reflected from the target volume of tissue:
            determine that a size of the target volume of tissue is greater than that associated with the first wavelength of the first optical signal;
            cause the light source to emit a second optical signal having a second wavelength that varies from the first wavelength of the first optical signal, the second optical signal forming a second returning optical signal; and
            determine whether the second returning optical signal has diffracted or reflected from the target volume of tissue;
        responsive to a determination that the second returning optical signal has diffracted from the target volume of tissue:
            determine that the size of the target volume of tissue is smaller than that associated with the second wavelength of the second optical signal; and
            determine a potential malignancy of the target volume of tissue based on a comparison between one or more spectral patterns of the first or second returning optical signal with one or more spectral patterns associated with malignant tissue;

wherein the receptacle comprises a curved and flexible outer surface that is adapted to accommodate at least a portion of the biomass via said direct contact therewith, the curved and flexible outer surface comprising the light source, the first light detector, and the second light detector each embedded to the curved and flexible outer surface of the receptacle.

2. The imaging system of claim 1, wherein the processing apparatus is further configured to determine the potential malignancy of the target volume of tissue based on a wavelength of the detected first returning optical signal.

3. The imaging system of claim 2, wherein:
the determination of the potential malignancy of the target volume of tissue is further based on a behavior of the detected first returning optical signal; and
the behavior of the detected first returning optical signal comprises diffraction, reflection, or fluorescence from the target volume of tissue.

4. The imaging system of claim 2, wherein the determination of the potential malignancy is further based on a comparison of the wavelength of the detected first returning optical signal with known values of wavelengths associated with malignant tissue.

5. The imaging system of claim 2, wherein the determination of the potential malignancy is further based on a comparison of the at least the wavelength of the detected first returning optical signal to a known parameter, the known parameter comprising a known diffraction pattern or an optical parameter.

6. The imaging system of claim 1, wherein the processing apparatus is further configured to:
cause a generation of an image of the target volume of tissue; and
cause a display of the generated image on a display screen.

7. The imaging system of claim 6, wherein:
the light source and the second light detector are each configured to convert between optical signals and electrical signals; and
the generation of the image is based at least in part on the electrical signals.

8. The imaging system of claim 1, wherein the light source and the second light detector are disposed proximate to an inner side of the outer surface of the receptacle.

9. The imaging system of claim 8, wherein the outer surface of the receptacle comprises an interface, the interface being configured to interface with a flexible layer positioned between the biomass and the interface, the flexible layer comprising a material composed so as to increase operational accuracy of the imaging system.

10. The imaging system of claim 1, wherein the assembly comprises a handheld device configured to be manually operated by a user, the manual operation comprising an adjustment of a position of the handheld device from an original position with respect to the biomass.

11. An apparatus for screening and diagnosis of breast cancer, the apparatus comprising:
a receptacle configured to directly contact a biomass;
a light source configured to emit one or more optical signals each comprising a plurality of wavelengths;
a first light detector and a second light detector each configured to detect returning optical signals and each configured to convert the returning optical signals to electrical signals; and
a processor apparatus configured to:
cause the light source to emit a first optical signal, the first optical signal having a first wavelength, thereby causing an emission of a first returning optical signal from interaction with a target volume of tissue, the target volume of tissue being a portion of the biomass;
determine whether the first returning optical signal has diffracted or reflected from the target volume of tissue based on the first returning optical signal from the target volume of tissue being detected by either or both of the first light detector and the second light detector;
based on a determination that the first returning optical signal has reflected from the target volume of tissue:
determine a size of the target volume of tissue as being greater than that associated with the first wavelength;
cause the light source to emit a second optical signal having a second wavelength that is different from the first wavelength, thereby causing an emission of a second returning optical signal from interaction with the target volume of tissue; and
determine whether the second returning optical signal has diffracted or reflected from the target volume of tissue;
based on a determination that the second returning optical signal has diffracted from the target volume of tissue, determine the size of the target volume of tissue as being smaller than that associated with the second wavelength; and
determine a potential malignancy of the target volume of tissue based on a comparison between a spectral pattern of the first or second returning optical signal with a spectral pattern associated with malignant tissue;
wherein the receptacle comprises a curved and flexible outer surface that is adapted to accommodate at least a portion of the biomass via said direct contact therewith, the curved and flexible outer surface comprising the light source, the first light detector, and the second light detector each embedded to the curved and flexible outer surface of the receptacle.

12. The apparatus of claim 11, wherein the processor apparatus is further configured to:
cause a generation of an image of the target volume of tissue based at least on the first returning optical signal or the second returning optical signal; and
cause a display of the generated image on a display apparatus.

13. The apparatus of claim 11, wherein the outer surface of the receptacle is configured to interface with a flexible layer positioned between the biomass and the outer surface, the flexible layer comprising a material composed so as to increase operational accuracy of the apparatus.

14. The apparatus of claim 11, wherein the light source, the first light detector, and the second light detector are disposed proximate to an inner side of the outer surface of the receptacle.

15. The apparatus of claim 11, wherein the apparatus comprises a handheld device configured to be manually operated by a user, the manual operation comprising an adjustment of a position of the handheld device from an original position with respect to the biomass.

16. A method for screening and diagnosis of breast cancer, the method comprising:
causing a light source of an imaging apparatus to emit a first optical signal, the imaging apparatus comprising a receptacle configured to directly contact a biomass, the receptacle comprising a curved and flexible outer surface adapted to accommodate at least a portion of the biomass via the direct contact therewith, the outer surface comprising the light source, a first light detector, and a second light detector each embedded to the outer surface, the light source being configured to emit one or more optical signals each comprising a plurality of wavelengths, the first optical signal having a first wavelength;

causing an emission of a first returning optical signal from interaction of the emitted first optical signal with a target volume of tissue from a biomass;

determining whether the first returning optical signal has diffracted or reflected from the target volume of tissue based on the first returning optical signal being detected by either or both of the first light detector and the second light detector of the imaging apparatus;

in response to a determination that the first returning optical signal has reflected from the target volume of tissue:

determining that a size of the target volume of tissue is greater than that associated with the first wavelength of the first optical signal;

causing the light source to emit a second optical signal having a second wavelength that varies from the first wavelength;

causing an emission of a second returning optical signal from interaction of the emitted second optical signal with the target volume of tissue; and determining whether the second returning optical signal has diffracted or reflected from the target volume of tissue;

in response to a determination that the second returning optical signal has diffracted from the target volume of tissue, determining that the size of the target volume of tissue is smaller than that associated with the second wavelength of the second optical signal; and determining a potential malignancy of the target volume of tissue based on a comparison between a spectral pattern of the first or second returning optical signal with a spectral pattern associated with malignant tissue.

17. The method of claim 16, further comprising:

causing the first returning optical signal to be converted to at least a first electrical signal; and causing the second returning optical signal to be converted to at least a second electrical signal.

18. The method of claim 17, further comprising:

causing an image of the target volume of tissue to be produced based on one or more of the at least first electrical signal and the at least second electrical signal; and causing the produced image to be rendered on a display.

19. The method of claim 16, wherein the determining of the potential malignancy of the target volume of tissue comprises determining whether the target volume of tissue comprises benign tumor tissue, calcified tissue, or active tumor tissue.

* * * * *